United States Patent
Davis et al.

(10) Patent No.: US 7,063,965 B2
(45) Date of Patent: *Jun. 20, 2006

(54) NUCLEIC ACID ENCODING TIE-2 LIGAND

(75) Inventors: Samuel Davis, New York, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 331 days.

This patent is subject to a terminal disclaimer.

(21) Appl. No.: 10/603,293

(22) Filed: Jun. 25, 2003

(65) Prior Publication Data

US 2005/0100906 A1    May 12, 2005

Related U.S. Application Data

(60) Division of application No. 09/442,717, filed on Nov. 18, 1999, now Pat. No. 6,627,415, which is a continuation of application No. 08/930,721, filed as application No. PCT/US96/04806 on Apr. 5, 1996, now abandoned.

(51) Int. Cl.
C12N 15/12    (2006.01)
C12N 5/10    (2006.01)
C12N 15/63    (2006.01)

(52) U.S. Cl. .................... 435/69.5; 435/70.1; 435/325; 435/471; 435/252.3; 435/254.11; 435/320.1; 536/23.1; 536/23.5

(58) Field of Classification Search .................. None
See application file for complete search history.

(56) References Cited

U.S. PATENT DOCUMENTS 5,116,964 A * 5/1992 Capon et al. ............. 536/23.5
5,332,671 A   7/1994 Ferrara et al.
5,521,073 A   5/1996 Davis et al.
5,643,755 A   7/1997 Davis et al.
5,650,490 A   7/1997 Davis et al.
5,814,464 A   9/1998 Davis et al.
5,879,672 A   3/1999 Davis et al.

FOREIGN PATENT DOCUMENTS

EP    0550296 A2    7/1993
WO    WO95/26364    10/1995

OTHER PUBLICATIONS

Banai, et al., Circulation, 1994, 89:2183-2189.
Unger, et al., Am. J. Physiol., 1994, 266:H1588-H1595.
Lazarous, et al., Circulation, 1995, 91:145-153.
Burrows, F. and Thorpe, P., PNAS (USA) 1993, 90:8996-9000.

* cited by examiner

Primary Examiner—Prema Mertz
(74) Attorney, Agent, or Firm—Valeta Gregg, Esq.; Ying-Zi Yang

(57) ABSTRACT

The present invention provides for an isolated nucleic acid molecule encoding a human TIE-2 ligand. In addition, the invention provides for a receptorbody which specifically binds a human TIE-2 ligand. The invention also provides an antibody which specifically binds a human TIE-2 ligand. The invention further provides for an antagonist of human TIE-2. The invention further provides for a ligandbody which specifically binds TIE-2 receptor. The invention also provides for therapeutic compositions as well as a method of blocking blood vessel growth, a method of promoting neovascularization, a method of promoting the growth, differentiation or migration of cells expressing the TIE-2 receptor, including, but not limited to, hematopoietic precursor cells, a method of blocking the growth, differentiation or migration of cells expressing the TIE-2 receptor including, but not limited to, hematopoietic precursor cells, and a method of attenuating or preventing tumor growth in a human.

9 Claims, 33 Drawing Sheets r EHK-1 ecto/h IgG1 Fc
Gelfoam (6ug)

r TIE-2 ecto/h IgG1 Fc
Gelfoam (6ug)

Fig. 4A

```
          10        20        30        40        50        60        70        80
           *         *         *         *         *         *         *         *
CAGCTGACTCAGGCAGGCTCCATGCTGAACGGTCACACAGAGAGGAAACAATAAATCTCAGCTACTATGCAATAAATATC 90       100       110       120       130       140       150       160
           *         *         *         *         *         *         *         *
TCAAGTTTTAACGAAGAAAAACATCATTGCAGTGAAATAAAAAATTTAAAATTTTAGAACAAAGCTAACAAATGGCTAG 170       180       190       200       210       220       230       240
           *         *         *         *         *         *         *         *
TTTTCTATGATTCTTCTTCAAACGCTTTCTTTGAGGGGAAAGAGTCAAACAAACAAGCAGTTTTACCTGAAATAAAGAA 250       260       270       280       290       300       310
           *         *         *         *         *         *         *
CTAGTTTTAGAGGTCAGAAGAAGGAGCAAGTTTGCGAGAGGCACGGAAGGAGTGTGCTGGCAGTACA ATG ACA GTT
                                                                     M   T   V  >

320               330                340                350                360                  370
  *                 *                  *                  *                  *                    *
TTC CTT TCC TTT GCT TTC CTC GCT GCC ATT CTG ACT CAC ATA GGG TGC AGC AAT CAG CGC
 F   L   S   F   A   F   L   A   A   I   L   T   H   I   G   C   S   N   Q   R >

380               390                400                410                420                  430
  *                 *                  *                  *                  *                    *
CGA AGT CCA GAA AAC AGT GGG AGA AGA TAT AAC CGG ATT CAA CAT GGG CAA TGT GCC TAC
 R   S   P   E   N   S   G   R   R   Y   N   R   I   Q   H   G   Q   C   A   Y >
```

Fig. 4B

```
440       450       460       470       480       490
 *         *         *         *         *         *
ACT TTC ATT CTT CCA GAA CAC GAT GGC AAC TGT CGT GAG AGT ACG ACA GAC CAG TAC AAC
 T   F   I   L   P   E   H   D   G   N   C   R   E   S   T   T   D   Q   Y   N 500       510       520       530       540       550
 *         *         *         *         *         *
ACA AAC GCT CTG CAG AGA GAT GCT CCA CAC GTG GAA CCG GAT TTC TCT TCC CAG AAA CTT
 T   N   A   L   Q   R   D   A   P   H   V   E   P   D   F   S   S   Q   K   L 560       570       580       590       600       610
 *         *         *         *         *         *
CAA CAT CTG GAA CAT GTG ATG AAT TAT ACT CAG TGG CTG CAA AAA CTT CAG GAG AAT TAC
 Q   H   L   E   H   V   M   E   N   Y   T   Q   W   L   Q   K   L   Q   E   N   Y 620       630       640       650       660       670
 *         *         *         *         *         *
ATT GTG GAA AAC ATG AAG TCG GAG ATG GCC CAG ATA CAG CTG CAA AAA CTT CAG GAG AAT TAC
 I   V   E   N   M   K   S   E   M   A   Q   I   Q   L   Q   N   A   V   Q   N   H 680       690       700       710       720       730
 *         *         *         *         *         *
ACG GCT ACC ATG CTG GAG ATA GGA ACC AGC CTC CTC TCT CAG ACT GCA GAG CAG ACC AGA
 T   A   T   M   L   E   I   G   T   S   L   L   S   Q   T   A   E   Q   T   R
```

Fig. 4C

```
740         750         760         770         780         790
 *           *           *           *           *           *
AAG CTG ACA GAT GTT GAG ACC CAG GTA CTA AAT CAA ACT TCT CGA CTT GAG ATA CAG CTG
 K   L   T   D   V   E   T   Q   V   L   N   Q   T   S   R   L   E   I   Q   L>

800         810         820         830         840         850
 *           *           *           *           *           *
CTG GAG AAT TCA TTA TCC ACC TAC AAG CTA TTA GAG AAG CAA CTT CTT CAA ACA AAT GAA
 L   E   N   S   L   S   T   Y   K   L   L   E   K   Q   L   L   Q   T   N   E>

860         870         880         890         900         910
 *           *           *           *           *           *
ATC TTG AAG ATC CAT GAA AAA AAC AGT TTA GAA CAT TTA GAA AAA ATC TTA GAA ATG GAA
 I   L   K   I   H   E   K   N   S   L   E   H   L   E   K   I   L   E   M   G>

920         930         940         950         960         970
 *           *           *           *           *           *
AAA CAC AAG GAA GAG TTG GAC ACC TTA AAG GAA GAA AAG GAG AAC CTT CAA GGC TTG GTT
 K   H   K   E   E   L   D   T   L   K   E   E   K   E   N   L   Q   G   L   V>

980         990         1000        1010        1020        1030
 *           *           *           *           *           *
ACT CGT CAA ACA TAT ATA ATC CAG GAG CTG GAA AAG CAA TTA AAC AGA GCT ACC AAC
 T   R   Q   T   Y   I   I   Q   E   L   E   K   Q   L   N   R   A   T   N>
```

Fig. 4D

```
1040        1050        1060        1070        1080        1090
 *           *           *           *           *           *
AAC AGT GTC CTT CAG AAG CAG CAA CTG GAG CTG ATG GAC ACA GTC CAC AAC CTT GTC AAT
 N   S   V   L   Q   K   Q   Q   L   E   L   M   D   T   V   H   N   L   V   N>

1100        1110        1120        1130        1140        1150
 *           *           *           *           *           *
CTT TGC ACT AAA GAA GGT GTT TTA CTA AAG GGA GGA AAA AGA GAG GAA GAG AAA CCA TTT
 L   C   T   K   E   G   V   L   L   K   G   G   K   R   E   E   E   K   P   F>

1160        1170        1180        1190        1200        1210
 *           *           *           *           *           *
AGA GAC TGT GCA GAT GTA TAT CAA GCT GGT TTT AAT AAA AGT GGA ATC TAC ACT ATT TAT
 R   D   C   A   D   V   Y   Q   A   G   F   N   K   S   G   I   Y   T   I   Y>

1220        1230        1240        1250        1260        1270
 *           *           *           *           *           *
ATT AAT AAT ATG CCA GAA CCC AAA AAG GTG TTT TGC AAT ATG GAT GTC AAT GGG GGA GGT
 I   N   N   M   P   E   P   K   K   V   F   C   N   M   D   V   N   G   G   G>

1280        1290        1300        1310        1320        1330
 *           *           *           *           *           *
TGG ACT GTA ATA CAA CAT CGT GAA GAT GGA AGT CTA GAT TTC CAA AGA GGC TGG AAG GAA
 W   T   V   I   Q   H   R   E   D   G   S   L   D   F   Q   R   G   W   K   E>

1340        1350        1360        1370        1380        1390
 *           *           *           *           *           *
TAT AAA ATG GGT TTT GGA AAT CCC TCC GGT GAA TAT TGG CTG GGG AAT GAG TTT ATT TTT
 Y   K   M   G   F   G   N   P   S   G   E   Y   W   L   G   N   E   F   I   F>
```

Fig. 4E

```
  1400      1410      1420      1430      1440      1450
   *         *         *         *         *         *
GCC ATT ACC AGT CAG AGG CAG TAC ATG CTA AGA ATT GAG TTA ATG GAC TGG GAA GGG AAC
 A   I   T   S   Q   R   Q   Y   M   L   R   I   E   L   M   D   W   E   G   N>

1460      1470      1480      1490      1500      1510
   *         *         *         *         *         *
CGA GCC TAT TCA CAG TAT GAC AGA TTC CAC ATA GGA TTT GAA AAG CAA AAC TAT AGG TTG
 R   A   Y   S   Q   Y   D   R   F   H   I   G   F   E   K   Q   N   Y   R   L>

1520      1530      1540      1550      1560      1570
   *         *         *         *         *         *
TAT TTA AAA GGT CAC ACT GGG ACA GCA GGA AAA CAG AGC CTG ATC TTA CAC GGT GCT
 Y   L   K   G   H   T   G   T   A   G   K   Q   S   L   I   L   H   G   A>

1580      1590      1600      1610      1620      1630
   *         *         *         *         *         *
GAT TTC AGC ACT AAA GAT GCT GAT AAT GAC AAC TGT ATG TGC AAA TGT GCC CTC ATG TTA
 D   F   S   T   K   D   A   D   N   D   N   C   M   C   K   C   A   L   M   L>

1640      1650      1660      1670      1680      1690
   *         *         *         *         *         *
ACA GGA TGG TGG TTT GAT GCT TGT GGC CCC TCC AAT CTA AAT GGA ATG TTC TAT ACT
 T   G   W   W   F   D   A   C   G   P   S   N   L   N   G   M   F   Y   T>
```

Fig. 4F

```
1700        1710        1720        1730        1740        1750
 *           *           *           *           *           *
GCG GGA CAA AAC CAT GGA AAA CTG AAT GGG ATA AAG TGG CAC TAC TTC AAA GGG CCC AGT
 A   G   Q   N   H   G   K   L   N   G   I   K   W   H   Y   F   K   G   P   S >

1760        1770        1780        1790        1800
             *           *           *           *           *
TAC TCC TTA CGT TCC ACA ACT ATG ATT CGA CCT TTA GAT TTT TGA
 Y   S   L   R   S   T   T   M   I   R   P   L   D   F   * >

1810        1820        1830        1840
 *           *           *           *
AAGGCCAATGTCAGAAGCGATTATGAAAGCAACA 1850        1860        1870        1880        1890        1900        1910        1920
             *           *           *           *           *           *           *           *
AAGAAATCCGAGAAGCTGCCAGGTGAGAAACTGTTTGAAAAACTTCAGAAGCAAACAATATTGTCTCCCTTCCAGCAATA 1930        1940        1950        1960        1970        1980        1990        2000
             *           *           *           *           *           *           *           *
AGTGGTAGTTATGTGAAGTCACCAAGGTTCTTGACCGTGAATCTGGAGCCGTTGAGTTCACAAGAGTCTCTACTTGGGG 2010        2020        2030        2040        2050        2060        2070        2080
             *           *           *           *           *           *           *           *
TGACAGTGCTGCTCACGTGGCTCGACTATAGAAAACTCCACTGACTGTCGGGCTTTAAAAAGGGAAGAAACTGCTGAGCTTGC 2090        2100        2110        2120        2130        2140
             *           *           *           *           *           *
TGTGCTTCAAACTACTACTGGACCTTATTTTGGAACTATGGTAGCCAGATGATAAATATGGTTAATTTC
```

Fig. 5A

```
         10         20         30         40         50         60         70         80
          *          *          *          *          *          *          *          *
CAGCTGACTCAGGCAGGCTCCATGCTGAACGGTCACACAGAGAGGAAACAATAAATCTCAGCTACTATGCAATAAATATC 90        100        110        120        130        140        150        160
          *          *          *          *          *          *          *          *
TCAAGTTTTAACGAAGAAAAACATCATTGCAGTGAAATAAAAATTTTAAAATTTTAGAACAAGCTAACAAATGGCTAG 170        180        190        200        210        220        230        240
          *          *          *          *          *          *          *          *
TTTTCTATGATTCTTCTTCAAACGCTTTCTTTGAGGGGAAAGAGTCAAACAAACAAGCAGTTTTACCTGAAATAAAGAA 250        260        270        280        290        300        310
          *          *          *          *          *          *          *
CTAGTTTTAGAGGTCAGAAGAAAAGGAGCAAGTTTTGCGAGAGGCACGGAAGGAGTGTGCTGGCAGTACA ATG ACA GTT
                                                                        M   T   V>

320                                  330                                        340                                        350                                        360                                        370
 *                                    *                                          *                                          *                                          *                                          *
TTC CTT TCC TTT GCT TTC CTC GCT GCC ATT CTG ACT CAC ATA GGG TGC AGC AAT CAG CGC
 F   L   S   F   A   F   L   A   A   I   L   T   H   I   G   C   S   N   Q   R>

380                                  390                                        400                                        410                                        420                                        430
 *                                    *                                          *                                          *                                          *                                          *
CGA AGT CCA GAA AAC AGT GGG AGA AGA TAT AAC CGG ATT CAA CAT GGG CAA TGT GCC TAC
 R   S   P   E   N   S   G   R   R   Y   N   R   I   Q   H   G   Q   C   A   Y>
```

Fig. 5B

```
440          450          460          470          480          490
 *            *            *            *            *            *
ACT TTC ATT CTT CCA GAA CAC GAT GGC AAC AGT ACG ACA GAC CAG TAC AAC
 T   F   I   L   P   E   H   D   G   N   S   T   T   D   Q   Y   N>

500          510          520          530          540          550
 *            *            *            *            *            *
ACA AAC GCT CTG CAG AGA GAT GCT CCA CAC GAA CCG GTG GAA AGT ACG GAT TTC TCT TCC CAG AAA CTT
 T   N   A   L   Q   R   D   A   P   H   E   P   V   E   S   T   D   F   S   S   Q   K   L>

560          570          580          590          600          610
 *            *            *            *            *            *
CAA CAT CTG GAA CAT GTG ATG GAA AAT TAT GAA AAT ATA CAG TGG CTG CAA
 Q   H   L   E   H   V   M   E   N   Y   E   N   I   Q   W   L   Q>

620          630          640          650          660          670
 *            *            *            *            *            *
ATT GTG GAA AAC ATG CTG GAA ATG AAG TCG GAG ATG GCC CAG ATA CAG CAG AAT GCA GTT CAG AAC CAC
 I   V   E   N   M   L   E   M   K   S   E   M   A   Q   I   Q   Q   N   A   V   Q   N   H>

680          690          700          710          720          730
 *            *            *            *            *            *
ACG GCT ACC ATG CTG GAG ATA GGA ACC AGC CTC TCT CAG CAG ACT GCA GAG CAG ACC AGA
 T   A   T   M   L   E   I   G   T   S   L   S   Q   Q   T   A   E   Q   T   R>

740          750          760          770          780          790
 *            *            *            *            *            *
AAG CTG ACA GAT GTT GAG ACC ATG CAG GTA CTA CTT TCT CGA CTT GAG ATA CAG CTG
 K   L   T   D   V   E   T   M   Q   V   L   L   S   R   L   E   I   Q   L>
```

Fig. 5C

```
800         810         820         830         840         850
 *           *           *           *           *           *
CTG GAG AAT TCA TTA TCC ACC TAC AAG CTA GAG AAG CAA CTT CTT CAA CAG ACA AAT GAA
 L   E   N   S   L   S   T   Y   K   L   E   K   Q   L   L   Q   Q   T   N   E>

860         870         880         890         900         910
 *           *           *           *           *           *
ATC TTG AAG ATC CAT GAA AAA AAC AGT TTA GAA CAT AAA ATC TTA GAA ATG GAA GGA
 I   L   K   I   H   E   K   N   S   L   E   H   K   I   L   E   M   E   G>

920         930         940         950         960         970
 *           *           *           *           *           *
AAA CAC AAG GAA GAG TTG GAC ACC TTA AAG GAA GAG AAA GAG AAC CTT CAA GGC TTG GTT
 K   H   K   E   E   L   D   T   L   K   E   E   K   E   N   L   Q   G   L   V>

980         990         1000        1010        1020        1030
 *           *           *           *           *           *
ACT CGT CAA ACA TAT ATA ATC CTT CAG AAG CAG CAA CTG GAG CTG ATG GAC ACA GTC CAC AAC ACC AAC
 T   R   Q   T   Y   I   I   L   Q   K   Q   Q   L   E   L   M   D   T   V   H   N   R   A   T   N>

1040        1050        1060        1070        1080        1090
 *           *           *           *           *           *
AAC AGT GTC CTT CAG AAG CAG CAA CTG GAG CTG ATG GAC ACA GTC CAC AAC CTT GTC AAT
 N   S   V   L   Q   K   Q   Q   L   E   L   M   D   T   V   H   N   L   V   N>

1100        1110        1120        1130        1140        1150
 *           *           *           *           *           *
CTT TGC ACT AAA GAA GTT TTA CTA AAG GGA GGA AAA AGA GAA GAG AAA CCA TTT AGA
 L   C   T   K   E   V   L   L   K   G   G   K   R   E   E   K   P   F   R>
```

Fig. 5D

```
          1160           1170           1180           1190           1200           1210
            *              *              *              *              *              *
         GAC TGT GCA GAT GTA TAT CAA GCT GGT TTT AAT AAA AGT GGA ATC TAC ACT ATT TAT ATT
          D   C   A   D   V   Y   Q   A   G   F   N   K   S   G   I   Y   T   I   Y   I>

1220           1230           1240           1250           1260           1270
            *              *              *              *              *              *
         AAT AAT ATG CCA GAA CCC AAA AAG GTG TTT TGC AAT ATG GAT GTC AAT GGG GGA GGT TGG
          N   N   M   P   E   P   K   K   V   F   C   N   M   D   V   N   G   G   G   W>

1280           1290           1300           1310           1320           1330
            *              *              *              *              *              *
         ACT GTA ATA CAA CAT CGT GAA GAT GGA AGT CTA GAT TTC CAA AGA GGC TGG AAG GAA TAT
          T   V   I   Q   H   R   E   D   G   S   L   D   F   Q   R   G   W   K   E   Y>

1340           1350           1360           1370           1380           1390
            *              *              *              *              *              *
         AAA ATG GGT TTT GGA AAT CCC TCC GGT GAA TAT TGG CTG GGG AAT GAG TTT ATT TTT GCC
          K   M   G   F   G   N   P   S   G   E   Y   W   L   G   N   E   F   I   F   A>

1400           1410           1420           1430           1440           1450
            *              *              *              *              *              *
         ATT ACC AGT CAG AGG CAG TAC ATG CTA AGA ATT GAG TTA ATG GAC TGG GAA GGG AAC CGA
          I   T   S   Q   R   Q   Y   M   L   R   I   E   L   M   D   W   E   G   N   R>

1460           1470           1480           1490           1500           1510
            *              *              *              *              *              *
         GCC TAT TCA CAG TAT GAC AGA TTC CAC ATA GGA AAT GAA AAG CAA AAC TAT AGG TTG TAT
          A   Y   S   Q   Y   D   R   F   H   I   G   N   E   K   Q   N   Y   R   L   Y>
```

Fig. 5E

```
     1520       1530       1540       1550       1560       1570
      *          *          *          *          *          *
TTA AAA GGT CAC ACT GGG ACA GCA GGA AAA CAG AGC AGC CTG ATC TTA CAC GGT GCT GAT
 L   K   G   H   T   G   T   A   G   K   Q   S   S   L   I   L   H   G   A   D>

1580       1590       1600       1610       1620       1630
      *          *          *          *          *          *
TTC AGC ACT AAA GAT GCT GAT AAT GAC AAC TGT ATG GCC CTC ATG TTA ACA
 F   S   T   K   D   A   D   N   D   N   C   M   A   L   M   L   T>

1640       1650       1660       1670       1680       1690
      *          *          *          *          *          *
GGA TGG TTT GAT GCT TGT GGC CCC AAT CTA AAT GGA ATG TTC TAT ACT GCG
 G   W   F   D   A   C   G   P   N   L   N   G   M   F   Y   T   A>

1700       1710       1720       1730       1740       1750
      *          *          *          *          *          *
GGA CAA AAC CAT GGA AAA CTG AAT GGG ATA AAG TGG CAC TAC TTC AAA GGG CCC AGT TAC
 G   Q   N   H   G   K   L   N   G   I   K   W   H   Y   F   K   G   P   S   Y>

1760       1770       1780       1790       1800
      *          *          *          *          *
TCC TTA CGT TCC ACA ACT ATG ATG ATT CGA CCT TTA GAT TTT TGA
 S   L   R   S   T   T   M   M   I   R   P   L   D   F   *>
```

Fig. 5F

```
            1810      1820      1830      1840
              *         *         *         *
AAGCGCAATGTCAGAAGCGATTATGAAAGCAACAAAG 1850      1860      1870      1880      1890      1900      1910      1920
         *         *         *         *         *         *         *         *
AAATCCGGAGAAGCTGCCAGGTGAGAAAACTGTTGAAAACTTCAGAAGCAAACAATATTGTCTCCCTTCCAGCAATAAGT 1930      1940      1950      1960      1970      1980      1990      2000
         *         *         *         *         *         *         *         *
GGTAGTTATGTGAAGTCACCAAGGTTCTTGACCGTGAATCTGGAGCCGTTTGAGTTCACAAGAGTCTCTACTTGGGGTGA 2010      2020      2030      2040      2050      2060      2070      2080
         *         *         *         *         *         *         *         *
CAGTGCTCACGTGGCTCGACTATAGAAAACTCCACTGACTGTCGGGCTTTAAAAAGGGAAGAAACTGCTGAGCTTGCTGT 2090      2100      2110      2120      2130      2140
         *         *         *         *         *         *
GCTTCAAACTACTACTGGACCTTATTTTGGAACTATGGTAGCCAGATGATAAATATGGTTAATTTC
```

Fig. 6A

```
          10         20         30         40         50         60         70         80
          *          *          *          *          *          *          *          *
GAATTCCTGGGGTTGGTGTTTATCTCCTCCCAGCCCTTGAGGGAGGAACACACTGTAGGATCTGGGGAGAGAGGAACAAA 90        100        110        120        130        140        150        160
          *          *          *          *          *          *          *          *
GGACCGTGAAAGCTGCTCTGTAAAAGCTGACACAGCCCTCCCAAGTGAGCAGGACTGTTCTCCCACTGCAATCTGACAG 170        180        190        200        210        220        230        240
          *          *          *          *          *          *          *          *
TTTTACTGCATGCCTGAGAGAACACAGCAGTAAAAAACCAGGTTTGCTACTGGAAAAAGAGAAAGAGAAGACTTTCATTG 250        260        270        280        290        300        310        320
          *          *          *          *          *          *          *          *
ACGGACCCAGCCATGGCAGCGTAGCAGCCCTGCGTTTCAGACGGCAGCAGCTCGGGACTCTGGACGTGTGTTTGCCCTCA 330        340        350        360        370        380
          *          *          *          *          *          *
AGTTTGCTAAGCTGCTGGTTTATTACTGAAGAAAGA ATG TGG CAG ATT GTT TTC TTT ACT CTG AGC TGT
                                      M   W   Q   I   V   F   F   T   L   S   C>

390        400        410        420        430        440
 *          *          *          *          *          *
GAT CTT GTC TTG GCC GCA GCC TAT AAC AAC TTT CGG AAG AGC ATG GAC AGC ATA GGA AAG
 D   L   V   L   A   A   A   Y   N   N   F   R   K   S   M   D   S   I   G   K>

450        460        470        480        490        500
 *          *          *          *          *          *
AAG CAA TAT CAG GTC CAG CAT GGG TCC TGC AGC TAC TTC CTC CTG CCA GAG ATG GAC
 K   Q   Y   Q   V   Q   H   G   S   C   S   Y   F   L   L   P   E   M   D>
```

Fig. 6B

```
510        520           530           540              550           560
 *          *             *             *                *             *
AAC TGC CGC TCT TCC TCC AGC CCC TAC GTG TCC AAT GCT GTG CAG AGG GAC GCG CCG CTC
 N   C   R   S   S   S   S   P   Y   V   S   N   A   V   Q   R   D   A   P   L>

570        580           590           600              610           620
 *          *             *             *                *             *
GAA TAC GAT GAC TCG GTG AGC CCC... 
```

[Figure 6B: DNA and protein sequence alignment spanning nucleotide positions 510–860, showing codons and their corresponding single-letter amino acid translations.]

Sequence (codon / amino acid) by position:

- 510: AAC (N), TGC (C), CGC (R)
- 520: TCT (S), TCC (S), TCC (S)
- 530: AGC (S), CCC (P), TAC (Y)
- 540: GTG (V), TCC (S), AAT (N), GCT (A)
- 550: GTG (V), CAG (Q), AGG (R)
- 560: GAC (D), GCG (A), CCG (P), CTC (L)
- 570: GAA (E), TAC (Y), GAT (D)
- 580: GAC (D), TCG (S), GTG (V)
- 590: AGC (S)... CCC (P)... TAC (Y)
- 600: CAA (Q), AGG (R), CTG (L), TCC (S)
- 610: GTG (V), CTG (L), GAG (E)
- 620: GAA (E), AAC (N), AAC (N), ACT (T)
- 630: CAG (Q), TGG (W), CTA (L)
- 640: ATG (M), AAG (K), CTT (L)
- 650: GAG (E), AAT (N), TAT (Y)
- 660: ATC (I), CAG (Q), GAC (D), AAC (N)
- 670: AAC (N), ATC (I), ATG (M)
- 680: GAA (E), ATG (M), GTA (V), GAG (E)
- 690: ATA (I), CAG (Q), CAG (Q)
- 700: AAT (N), GCA (A), GTA (V)
- 710: GAG (E), AAT (N), TAT (Y)
- 720: ATC (I), CAG (Q), ACG (T), GCT (A)
- 730: GTG (V), ATG (M), ATA (I)
- 740: AAG (K), AAA (K), ACA (T), AAC (N), CTG (L)
- 750: TTG (L), AAC (N), CAA (Q)
- 760: ACA (T), GCT (A), GTA (V)
- 770: GAG (E), ACG (T), CAA (Q)
- 780: AAG (K), TTA (L), ACT (T), GAT (D)
- 790: GTG (V), GAA (E), GCC (A)
- 800: CAA (Q), GTA (V), TTA (L), AAT (N)
- 810: CAG (Q), ACC (T), ACG (T)
- 820: AGA (R), CTT (L), GAA (E)
- 830: CAA (Q), ACG (T), CGG (R)
- 840: CTT (L), GAA (E), CAC (H), TCC (S)
- 850: CTC (L), TCG (S), ACA (T)
- 860: AAA (K), TTG (L), GAA (E)

Fig. 6C

```
 870                880         890         900         910         920
  *                  *           *           *           *           *
AAA CAG ATT TTG GAC CAG ACC AGT GAA ATA AAC AAA TTG CAA GAT AAG AAC AGT TTC CTA
 K   Q   I   L   D   Q   T   S   E   I   N   K   L   Q   D   K   N   S   F   L>

930                940         950         960         970         980
  *                  *           *           *           *           *
GAA AAG GTG CTA GCT ATG GAA GAC AAG CAC ATC CAA CTA CAG TCA ATA AAA GAA
 E   K   V   L   A   M   E   D   K   H   I   Q   L   Q   S   I   K   E>

990                1000        1010        1020        1030        1040
  *                  *           *           *           *           *
GAG AAA GAT CAG CTA CAG GTG TTA GTA TCC AAG CAA AAT TCC ATC ATT GAA GAA CTA GAA
 E   K   D   Q   L   Q   V   L   V   S   K   Q   N   S   I   I   E   E   L   E>

1050               1060        1070        1080        1090        1100
  *                  *           *           *           *           *
AAA ATA GTG ACT GCC ACG GTG AAT AAT TCA GTT CTT CAA AAG CAG CAA CAT GAT CTC
 K   I   V   T   A   T   V   N   N   S   V   L   Q   K   Q   Q   H   D   L>

1110               1120        1130        1140        1150        1160
  *                  *           *           *           *           *
ATG GAG ACA GTT AAT AAC TTA CTG ACT ATG TCC ACA TCA AAC TCA GCT AAG GAC CCC
 M   E   T   V   N   N   L   L   T   M   S   T   S   N   S   A   K   D   P>

1170               1180        1190        1200        1210        1220
  *                  *           *           *           *           *
ACT GTT GCT AAA GAA GAA CAA GAA ATC AGC TTC AGA GAC TGT GCT GAA GTA TTC AAA TCA GGA
 T   V   A   K   E   E   Q   E   I   S   F   R   D   C   A   E   V   F   K   S   G>
```

Fig. 6D

```
1230        1240        1250        1260        1270        1280
  *           *           *           *           *           *
CAC ACC ACA AAT GGC ATC TAC ACG TTA ACA TTC CCT AAT TCT ACA GAA GAG ATC AAG GCC
 H   T   T   N   G   I   Y   T   L   T   F   P   N   S   T   E   E   I   K   A>

1290        1300        1310        1320        1330        1340
  *           *           *           *           *           *
TAC TGT GAC ATG GAA GCT TAC ACG GGA GGA GGC TGG ACA ATT CAG CGA CGT GAG GAT GGC
 Y   C   D   M   E   A   Y   T   G   G   G   W   T   I   Q   R   R   E   D   G>

1350        1360        1370        1380        1390        1400
  *           *           *           *           *           *
AGC GTT GAT TTT CAG AGG ACT TGG AAA GTG GGA TAT ATT CAG CAA AAC CCT TCA GGA
 S   V   D   F   Q   R   T   W   K   V   G   Y   I   Q   Q   N   P   S   G>

1410        1420        1430        1440        1450        1460
  *           *           *           *           *           *
GAA TAT TGG CTG GGA AAT GAG TTT GTT TCG CAA CTG ACT AAT CAG CGC TAT GTG CTT
 E   Y   W   L   G   N   E   F   V   S   Q   L   T   N   Q   R   Y   V   L>

1470        1480        1490        1500        1510        1520
  *           *           *           *           *           *
AAA ATA CAC CTT AAA GAC TGG GAA AAT GGA GCT TAC TCA TTG TAT GAA CAT TTC TAT
 K   I   H   L   K   D   W   E   N   G   A   Y   S   L   Y   E   H   F   Y>

1530        1540        1550        1560        1570        1580
  *           *           *           *           *           *
CTC TCA AGT GAA GAA CTC AAT TAT AGG ATT CAC CTT AAA GGA CTT ACA GCC GGC
 L   S   S   E   E   L   N   Y   R   I   H   L   K   G   L   T   A   G>
```

Fig. 6E

```
1590        1600        1610        1620        1630        1640
 *           *           *           *           *           *
AAA ATA AGC AGC ATC AGC CAA CCA GGA AAT GAT TTT AGC ACA AAG GAT GGA GAC AAC GAC
 K   I   S   S   I   S   Q   P   G   N   D   F   S   T   K   D   G   D   N   D>

1650        1660        1670        1680        1690        1700
 *           *           *           *           *           *
AAA TGT ATT TGC AAA TGT TCA CAA ATG CTA ACA GGA GGC TGG TTT GAT GCA TGT GGT
 K   C   I   C   K   C   S   Q   M   L   T   G   G   W   F   D   A   C   G>

1710        1720        1730        1740        1750        1760
 *           *           *           *           *           *
CCT TCC AAC TTG AAC GGA ATG TAC TAT CCA CAG AGG CAG AAC ACA AAT AAG TTC AAC GGC
 P   S   N   L   N   G   M   Y   Y   P   Q   R   Q   N   T   N   K   F   N   G>

1770        1780        1790        1800        1810        1820
 *           *           *           *           *           *
ATT AAA TGG TAC TAC TGG AAA GGC TCA GGC TAT TCG CTC AAG GCC ACA ACC ATG ATG ATC
 I   K   W   Y   Y   W   K   G   S   G   Y   S   L   K   A   T   T   M   M   I>

1830        1840
 *           *
CGA CCA GCA GAT TTC
 R   P   A   D   F>

1850        1860        1870        1880        1890        1900        1910        1920
          *           *           *           *           *           *           *           *
TAAACATCCCAGTCCACCTGAGGAACTGTCTCGAACTATTTTCAAAGACTTAAGCCCAGTGCACTGAAAGTCACGG
```

Fig. 6F

```
         1930      1940      1950      1960      1970      1980      1990      2000
           *         *         *         *         *         *         *         *
CTGCGCACTGTGTCCTCTTCCACCACAGAGGGCGTGTCGGTGCTGGTGCTGAGGGACCCCACAGCTCCAGATTAGAGCCTGT 2010      2020      2030      2040      2050      2060      2070      2080
           *         *         *         *         *         *         *         *
AAACTTTATCACTTAAACTGCATCACTTAACGGACCAAAGCAAGACCCTAAACATCCATAATTGTGATTAGACAGAACA 2090      2100      2110      2120      2130      2140      2150      2160
           *         *         *         *         *         *         *         *
CCTATGCAAAGATGAACCCGAGGCTGAGAATCAGAACTGACAGTTTACAGACGCTGCTGTCACAACCAAGAATGTTATGTG 2170      2180      2190      2200      2210      2220      2230      2240
           *         *         *         *         *         *         *         *
CAAGTTTATCAGTAAATAACTGGAAAACAGAACACTTATGTTATACAATACAGATCATCTTGGAACTGCATTCTTCTGAG 2250      2260      2270      2280
           *         *         *         *
CACTGTTTATACACTGTGTAAATACCCATATGTCCTGAATTC
```

Fig. 11.
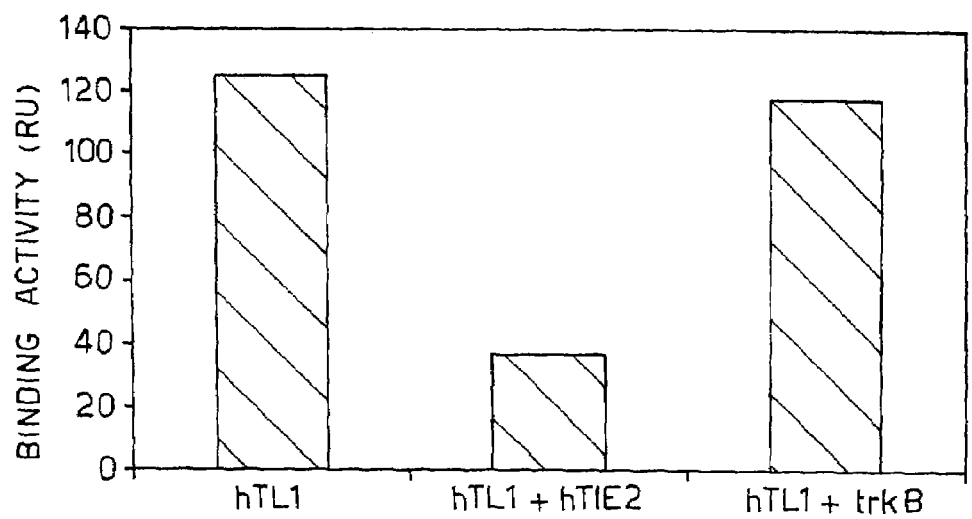
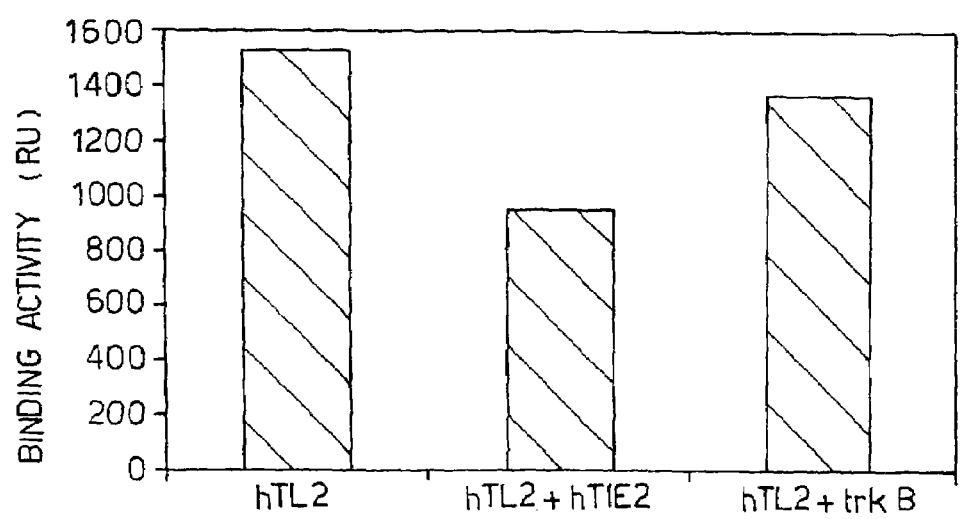

FL: Fetal Liver

Fetal Thymus E17.5

CDR1$^+$ : Cortical stromal cells

A2B5$^+$ : Medulla stromal cells

Fig. 17. ENGINEERING OF TIE2 "LIGAND-BODIES"

COVALENT MULTIMERIC STRUCTURE OF TL1 AND TL2 AND THEIR INTERCONVERSION BY THE MUTATION OF ONE CYSTEINE

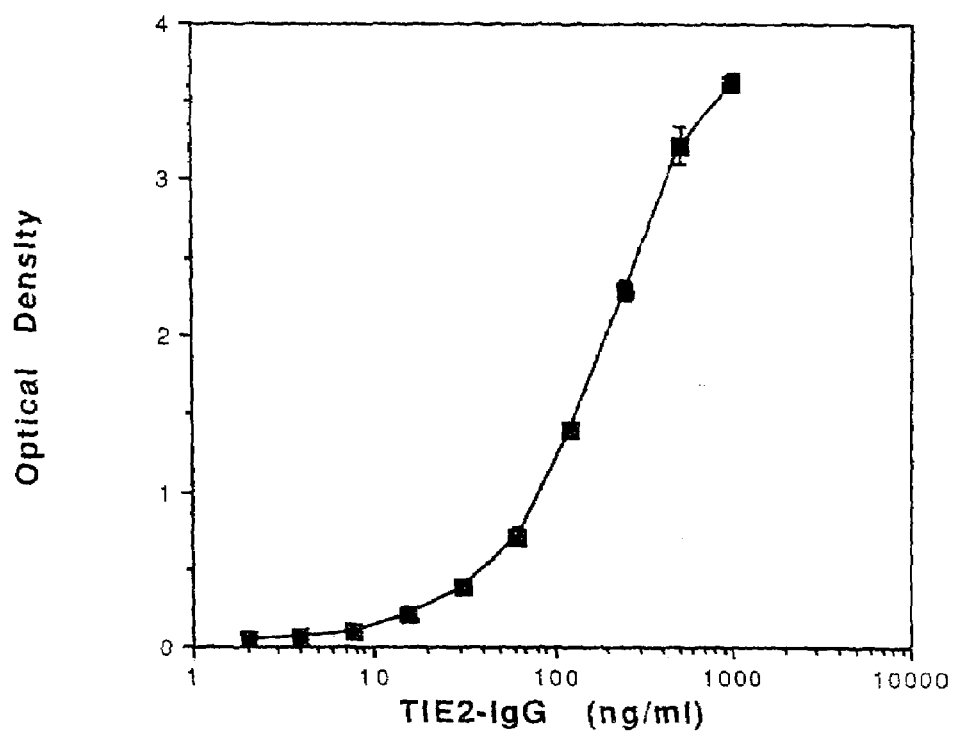
Fig.19. TIE2-IgG binding to immobilized TL1
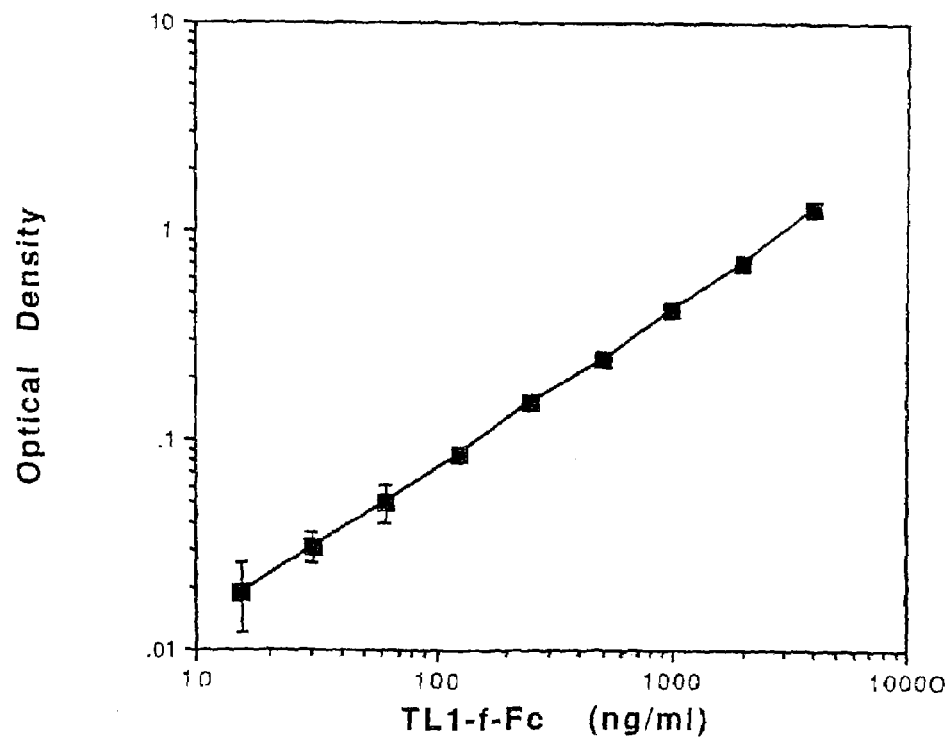
Fig.20. TL1-f-Fc binding to immobilized Tie2 ectodomain

SEQUENCE LISTING

```
<160> NUMBER OF SEQ ID NOS: 6

<210> SEQ ID NO 1
<211> LENGTH: 2149
<212> TYPE: DNA
<213> ORGANISM: Homo sapiens
<220> FEATURE:
<221> NAME/KEY: CDS
<222> LOCATION: (310)..(1803)

<400> SEQUENCE: 1
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
```

-continued

```
ctagttttag aggtcagaag aaaggagcaa gttttgcgag aggcacggaa ggagtgtgct          300 ggcagtaca atg aca gtt ttc ctt tcc ttt gct ttc ctc gct gcc att ctg         351
          Met Thr Val Phe Leu Ser Phe Ala Phe Leu Ala Ala Ile Leu
           1               5                  10 act cac ata ggg tgc agc aat cag cgc cga agt cca gaa aac agt ggg          399
Thr His Ile Gly Cys Ser Asn Gln Arg Arg Ser Pro Glu Asn Ser Gly
 15              20                  25                  30 aga aga tat aac cgg att caa cat ggg caa tgt gcc tac act ttc att          447
Arg Arg Tyr Asn Arg Ile Gln His Gly Gln Cys Ala Tyr Thr Phe Ile
             35                  40                  45 ctt cca gaa cac gat ggc aac tgt cgt gag agt acg aca gac cag tac          495
Leu Pro Glu His Asp Gly Asn Cys Arg Glu Ser Thr Thr Asp Gln Tyr
         50                  55                  60 aac aca aac gct ctg cag aga gat gct cca cac gtg gaa ccg gat ttc          543
Asn Thr Asn Ala Leu Gln Arg Asp Ala Pro His Val Glu Pro Asp Phe
             65                  70                  75 tct tcc cag aaa ctt caa cat ctg gaa cat gtg atg gaa aat tat act          591
Ser Ser Gln Lys Leu Gln His Leu Glu His Val Met Glu Asn Tyr Thr
     80                  85                  90 cag tgg ctg caa aaa ctt gag aat tac att gtg gaa aac atg aag tcg          639
Gln Trp Leu Gln Lys Leu Glu Asn Tyr Ile Val Glu Asn Met Lys Ser
 95                 100                 105                 110 gag atg gcc cag ata cag cag aat gca gtt cag aac cac acg gct acc          687
Glu Met Ala Gln Ile Gln Gln Asn Ala Val Gln Asn His Thr Ala Thr
             115                 120                 125 atg ctg gag ata gga acc agc ctc ctc tct cag act gca gag cag acc          735
Met Leu Glu Ile Gly Thr Ser Leu Leu Ser Gln Thr Ala Glu Gln Thr
         130                 135                 140 aga aag ctg aca gat gtt gag acc cag gta cta aat caa act tct cga          783
Arg Lys Leu Thr Asp Val Glu Thr Gln Val Leu Asn Gln Thr Ser Arg
             145                 150                 155 ctt gag ata cag ctg ctg gag aat tca tta tcc acc tac aag cta gag          831
Leu Glu Ile Gln Leu Leu Glu Asn Ser Leu Ser Thr Tyr Lys Leu Glu
         160                 165                 170 aag caa ctt ctt caa cag aca aat gaa atc ttg aag atc cat gaa aaa          879
Lys Gln Leu Leu Gln Gln Thr Asn Glu Ile Leu Lys Ile His Glu Lys
175                 180                 185                 190 aac agt tta tta gaa cat aaa atc tta gaa atg gaa gga aaa cac aag          927
Asn Ser Leu Leu Glu His Lys Ile Leu Glu Met Glu Gly Lys His Lys
                 195                 200                 205 gaa gag ttg gac acc tta aag gaa gag aaa gag aac ctt caa ggc ttg          975
Glu Glu Leu Asp Thr Leu Lys Glu Glu Lys Glu Asn Leu Gln Gly Leu
             210                 215                 220 gtt act cgt caa aca tat ata atc cag gag ctg gaa aag caa tta aac          1023
Val Thr Arg Gln Thr Tyr Ile Ile Gln Glu Leu Glu Lys Gln Leu Asn
             225                 230                 235 aga gct acc acc aac aac agt gtc ctt cag aag cag caa ctg gag ctg          1071
Arg Ala Thr Thr Asn Asn Ser Val Leu Gln Lys Gln Gln Leu Glu Leu
 240                 245                 250 atg gac aca gtc cac aac ctt gtc aat ctt tgc act aaa gaa ggt gtt          1119
Met Asp Thr Val His Asn Leu Val Asn Leu Cys Thr Lys Glu Gly Val
255                 260                 265                 270 tta cta aag gga gga aaa aga gag gaa gag aaa cca ttt aga gac tgt          1167
Leu Leu Lys Gly Gly Lys Arg Glu Glu Glu Lys Pro Phe Arg Asp Cys
                 275                 280                 285 gca gat gta tat caa gct ggt ttt aat aaa agt gga atc tac act att          1215
Ala Asp Val Tyr Gln Ala Gly Phe Asn Lys Ser Gly Ile Tyr Thr Ile
             290                 295                 300 tat att aat aat atg cca gaa ccc aaa aag gtg ttt tgc aat atg gat          1263
```

```
                                                           -continued
Tyr Ile Asn Asn Met Pro Glu Pro Lys Lys Val Phe Cys Asn Met Asp
            305                 310                 315 gtc aat ggg gga ggt tgg act gta ata caa cat cgt gaa gat gca agt      1311
Val Asn Gly Gly Gly Trp Thr Val Ile Gln His Arg Glu Asp Ala Ser
320                 325                 330 cta gat ttc caa aga ggc tgg aag gaa tat aaa atg ggt ttt gga aat      1359
Leu Asp Phe Gln Arg Gly Trp Lys Glu Tyr Lys Met Gly Phe Gly Asn
335                 340                 345                 350 ccc tcc ggt gaa tat tgg ctg ggg aat gag ttt att ttt gcc att acc      1407
Pro Ser Gly Glu Tyr Trp Leu Gly Asn Glu Phe Ile Phe Ala Ile Thr
                355                 360                 365 agt cag agg cag tac atg cta aga att gag tta atg gac tgg gaa ggg      1455
Ser Gln Arg Gln Tyr Met Leu Arg Ile Glu Leu Met Asp Trp Glu Gly
            370                 375                 380 aac cga gcc tat tca cag tat gac aga ttc cac ata gga aat gaa aag      1503
Asn Arg Ala Tyr Ser Gln Tyr Asp Arg Phe His Ile Gly Asn Glu Lys
        385                 390                 395 caa aac tat agg ttg tat tta aaa ggt cac act ggg aca gca gga aaa      1551
Gln Asn Tyr Arg Leu Tyr Leu Lys Gly His Thr Gly Thr Ala Gly Lys
    400                 405                 410 cag agc agc ctg atc tta cac ggt gct gat ttc agc act aaa gat gct      1599
Gln Ser Ser Leu Ile Leu His Gly Ala Asp Phe Ser Thr Lys Asp Ala
415                 420                 425                 430 gat aat gac aac tgt atg tgc aaa tgt gcc ctc atg tta aca gga gga      1647
Asp Asn Asp Asn Cys Met Cys Lys Cys Ala Leu Met Leu Thr Gly Gly
                435                 440                 445 tgg tgg ttt gat gct tgt ggc ccc tcc aat cta aat gga atg ttc tat      1695
Trp Trp Phe Asp Ala Cys Gly Pro Ser Asn Leu Asn Gly Met Phe Tyr
            450                 455                 460 act gcg gga caa aac cat gga aaa ctg aat ggg ata aag tgg cac tac      1743
Thr Ala Gly Gln Asn His Gly Lys Leu Asn Gly Ile Lys Trp His Tyr
        465                 470                 475 ttc aaa ggg ccc agt tac tcc tta cgt tcc aca act atg atg att cga      1791
Phe Lys Gly Pro Ser Tyr Ser Leu Arg Ser Thr Thr Met Met Ile Arg
    480                 485                 490 cct tta gat ttt tgaaagcgca atgtcagaag cgattatgaa agcaacaaag          1843
Pro Leu Asp Phe
495 aaatccggag aagctgccag gtgagaaact gtttgaaaac ttcagaagca acaatattg     1903 tctcccttcc agcaataagt ggtagttatg tgaagtcacc aaggttcttg accgtgaatc    1963 tggagccgtt tgagttcaca agagtctcta cttggggtga cagtgctcac gtggctcgac    2023 tatagaaaac tccactgact gtcgggcttt aaaaagggaa gaaactgctg agcttgctgt    2083 gcttcaaact actactggac cttattttgg aactatggta gccagatgat aaatatggtt    2143 aatttc                                                                2149

<210> SEQ ID NO 2
<211> LENGTH: 498
<212> TYPE: PRT
<213> ORGANISM: Homo sapiens

<400> SEQUENCE: 2

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45
```

```
Glu His Asp Gly Asn Cys Arg Glu Ser Thr Thr Asp Gln Tyr Asn Thr
    50                  55                  60
Asn Ala Leu Gln Arg Asp Ala Pro His Val Glu Pro Asp Phe Ser Ser
65                  70                  75                  80
Gln Lys Leu Gln His Leu Glu His Val Met Glu Asn Tyr Thr Gln Trp
                85                  90                  95
Leu Gln Lys Leu Glu Asn Tyr Ile Val Glu Asn Met Lys Ser Glu Met
            100                 105                 110
Ala Gln Ile Gln Gln Asn Ala Val Gln Asn His Thr Ala Thr Met Leu
            115                 120                 125
Glu Ile Gly Thr Ser Leu Leu Ser Gln Thr Ala Glu Gln Thr Arg Lys
    130                 135                 140
Leu Thr Asp Val Glu Thr Gln Val Leu Asn Gln Thr Ser Arg Leu Glu
145                 150                 155                 160
Ile Gln Leu Leu Glu Asn Ser Leu Ser Thr Tyr Lys Leu Glu Lys Gln
                165                 170                 175
Leu Leu Gln Gln Thr Asn Glu Ile Leu Lys Ile His Glu Lys Asn Ser
            180                 185                 190
Leu Leu Glu His Lys Ile Leu Glu Met Glu Gly Lys His Lys Glu Glu
            195                 200                 205
Leu Asp Thr Leu Lys Glu Glu Lys Glu Asn Leu Gln Gly Leu Val Thr
    210                 215                 220
Arg Gln Thr Tyr Ile Ile Gln Glu Leu Glu Lys Gln Leu Asn Arg Ala
225                 230                 235                 240
Thr Thr Asn Asn Ser Val Leu Gln Lys Gln Gln Leu Glu Leu Met Asp
                245                 250                 255
Thr Val His Asn Leu Val Asn Leu Cys Thr Lys Glu Gly Val Leu Leu
            260                 265                 270
Lys Gly Gly Lys Arg Glu Glu Lys Pro Phe Arg Asp Cys Ala Asp
            275                 280                 285
Val Tyr Gln Ala Gly Phe Asn Lys Ser Gly Ile Tyr Thr Ile Tyr Ile
    290                 295                 300
Asn Asn Met Pro Glu Pro Lys Lys Val Phe Cys Asn Met Asp Val Asn
305                 310                 315                 320
Gly Gly Gly Trp Thr Val Ile Gln His Arg Glu Asp Ala Ser Leu Asp
                325                 330                 335
Phe Gln Arg Gly Trp Lys Glu Tyr Lys Met Gly Phe Gly Asn Pro Ser
            340                 345                 350
Gly Glu Tyr Trp Leu Gly Asn Glu Phe Ile Phe Ala Ile Thr Ser Gln
            355                 360                 365
Arg Gln Tyr Met Leu Arg Ile Glu Leu Met Asp Trp Glu Gly Asn Arg
    370                 375                 380
Ala Tyr Ser Gln Tyr Asp Arg Phe His Ile Gly Asn Glu Lys Gln Asn
385                 390                 395                 400
Tyr Arg Leu Tyr Leu Lys Gly His Thr Gly Thr Ala Gly Lys Gln Ser
                405                 410                 415
Ser Leu Ile Leu His Gly Ala Asp Phe Ser Thr Lys Asp Ala Asp Asn
            420                 425                 430
Asp Asn Cys Met Cys Lys Cys Ala Leu Met Leu Thr Gly Gly Trp Trp
            435                 440                 445
Phe Asp Ala Cys Gly Pro Ser Asn Leu Asn Gly Met Phe Tyr Thr Ala
    450                 455                 460
```

```
Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 3
<211> LENGTH: 2146
<212> TYPE: DNA
<213> ORGANISM: Homo sapiens
<220> FEATURE:
<221> NAME/KEY: CDS
<222> LOCATION: (310)..(1800)

<400> SEQUENCE: 3
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300 ggcagtaca atg aca gtt ttc ctt tcc ttt gct ttc ctc gct gcc att ctg    351
          Met Thr Val Phe Leu Ser Phe Ala Phe Leu Ala Ala Ile Leu
            1               5                   10 act cac ata ggg tgc agc aat cag cgc cga agt cca gaa aac agt ggg        399
Thr His Ile Gly Cys Ser Asn Gln Arg Arg Ser Pro Glu Asn Ser Gly
 15                  20                  25                  30 aga aga tat aac cgg att caa cat ggg caa tgt gcc tac act ttc att        447
Arg Arg Tyr Asn Arg Ile Gln His Gly Gln Cys Ala Tyr Thr Phe Ile
                 35                  40                  45 ctt cca gaa cac gat ggc aac tgt cgt gag agt aca aca gac cag tac        495
Leu Pro Glu His Asp Gly Asn Cys Arg Glu Ser Thr Thr Asp Gln Tyr
             50                  55                  60 aac aca aac gct ctg cag aga gat gct cca cac gtg gaa ccg gat ttc        543
Asn Thr Asn Ala Leu Gln Arg Asp Ala Pro His Val Glu Pro Asp Phe
 65                  70                  75 tct tcc cag aaa ctt caa cat ctg gaa cat gtg atg gaa aat tat act        591
Ser Ser Gln Lys Leu Gln His Leu Glu His Val Met Glu Asn Tyr Thr
             80                  85                  90 cag tgg ctg caa aaa ctt gag aat tac att gtg gaa aac atg aag tcg        639
Gln Trp Leu Gln Lys Leu Glu Asn Tyr Ile Val Glu Asn Met Lys Ser
 95                 100                 105                 110 gag atg gcc cag ata cag cag aat gca gtt cag aac cac acg gct acc        687
Glu Met Ala Gln Ile Gln Gln Asn Ala Val Gln Asn His Thr Ala Thr
                115                 120                 125 atg ctg gag ata gga acc agc ctc ctc tct cag act gca gag cag acc        735
Met Leu Glu Ile Gly Thr Ser Leu Leu Ser Gln Thr Ala Glu Gln Thr
            130                 135                 140 aga aag ctg aca gat gtt gag acc cag gta cta aat caa act tct cga       783
Arg Lys Leu Thr Asp Val Glu Thr Gln Val Leu Asn Gln Thr Ser Arg
        145                 150                 155 ctt gag ata cag ctg ctg gag aat tca tta tcc acc tac aag cta gag       831
Leu Glu Ile Gln Leu Leu Glu Asn Ser Leu Ser Thr Tyr Lys Leu Glu
    160                 165                 170 aag caa ctt ctt caa cag aca aat gaa atc ttg aag atc cat gaa aaa       879
Lys Gln Leu Leu Gln Gln Thr Asn Glu Ile Leu Lys Ile His Glu Lys
175                 180                 185                 190 aac agt tta tta gaa cat aaa atc tta gaa atg gaa gga aaa cac aag       927
Asn Ser Leu Leu Glu His Lys Ile Leu Glu Met Glu Gly Lys His Lys
```

-continued

```
              195                 200                 205
gaa gag ttg gac acc tta aag gaa gag aaa gag aac ctt caa ggc ttg        975
Glu Glu Leu Asp Thr Leu Lys Glu Glu Lys Glu Asn Leu Gln Gly Leu
            210                 215                 220 gtt act cgt caa aca tat ata atc cag gag ctg gaa aag caa tta aac       1023
Val Thr Arg Gln Thr Tyr Ile Ile Gln Glu Leu Glu Lys Gln Leu Asn
        225                 230                 235 aga gct acc acc aac aac agt gtc ctt cag aag cag caa ctg gag ctg       1071
Arg Ala Thr Thr Asn Asn Ser Val Leu Gln Lys Gln Gln Leu Glu Leu
        240                 245                 250 atg gac aca gtc cac aac ctt gtc aat ctt tgc act aaa gaa gtt tta       1119
Met Asp Thr Val His Asn Leu Val Asn Leu Cys Thr Lys Glu Val Leu
255                 260                 265                 270 cta aag gga gga aaa aga gag gaa gac aaa cca ttt aga gac tgt gca       1167
Leu Lys Gly Gly Lys Arg Glu Glu Asp Lys Pro Phe Arg Asp Cys Ala
                275                 280                 285 gat gta tat caa gct ggt ttt aat aaa agt gga atc tac act att tat       1215
Asp Val Tyr Gln Ala Gly Phe Asn Lys Ser Gly Ile Tyr Thr Ile Tyr
            290                 295                 300 att aat aat atg cca gaa ccc aaa aag gtg ttt tgc aat atg gat gtc       1263
Ile Asn Asn Met Pro Glu Pro Lys Lys Val Phe Cys Asn Met Asp Val
        305                 310                 315 aat ggg gga ggt tgg act gta ata caa cat cgt gaa gat gga agt cta       1311
Asn Gly Gly Gly Trp Thr Val Ile Gln His Arg Glu Asp Gly Ser Leu
320                 325                 330 gat ttc caa aga ggc tgg aag gaa tat aaa atg ggt ttt gga aat ccc       1359
Asp Phe Gln Arg Gly Trp Lys Glu Tyr Lys Met Gly Phe Gly Asn Pro
335                 340                 345                 350 tcc ggt gaa tat tgg ctg ggg aat gag ttt att ttt gcc att acc agt       1407
Ser Gly Glu Tyr Trp Leu Gly Asn Glu Phe Ile Phe Ala Ile Thr Ser
                355                 360                 365 cag agg cag tac atg cta aga att gag tta atg gac tgg gaa ggg aac       1455
Gln Arg Gln Tyr Met Leu Arg Ile Glu Leu Met Asp Trp Glu Gly Asn
            370                 375                 380 cga gcc tat tca cag tat gac aga ttc cac ata gga aat gaa aag caa       1503
Arg Ala Tyr Ser Gln Tyr Asp Arg Phe His Ile Gly Asn Glu Lys Gln
        385                 390                 395 aac tat agg ttg tat tta aaa ggt cac act ggg aca gca gga aaa cag       1551
Asn Tyr Arg Leu Tyr Leu Lys Gly His Thr Gly Thr Ala Gly Lys Gln
        400                 405                 410 agc agc ctg atc tta cac ggt gct gat ttc agc act aaa gat gct gat       1599
Ser Ser Leu Ile Leu His Gly Ala Asp Phe Ser Thr Lys Asp Ala Asp
415                 420                 425                 430 aat gac aac tgt atg tgc aaa tgt gcc ctc atg tta aca gga gga tgg       1647
Asn Asp Asn Cys Met Cys Lys Cys Ala Leu Met Leu Thr Gly Gly Trp
                435                 440                 445 tgg ttt gat gct tgt ggc ccc tcc aat cta aat gga atg ttc tat act       1695
Trp Phe Asp Ala Cys Gly Pro Ser Asn Leu Asn Gly Met Phe Tyr Thr
            450                 455                 460 gcg gga caa aac cat gga aaa ctg aat ggg ata aag tgg cac tac ttc       1743
Ala Gly Gln Asn His Gly Lys Leu Asn Gly Ile Lys Trp His Tyr Phe
        465                 470                 475 aaa ggg ccc agt tac tcc tta cgt tcc aca act atg atg att cga cct       1791
Lys Gly Pro Ser Tyr Ser Leu Arg Ser Thr Thr Met Met Ile Arg Pro
        480                 485                 490 tta gat ttt tgaaagcgca atgtcagaag cgattatgaa agcaacaaag               1840
Leu Asp Phe
495 aaatccggag aagctgccag gtgagaaact gtttgaaaac ttcagaagca aacaatattg     1900
```

```
tctcccttcc agcaataagt ggtagttatg tgaagtcacc aaggttcttg accgtgaatc    1960
tggagccgtt tgagttcaca agagtctcta cttggggtga cagtgctcac gtggctcgac    2020
tatagaaaac tccactgact gtcgggcttt aaaaagggaa gaaactgctg agcttgctgt    2080
gcttcaaact actactggac cttatttttgg aactatggta gccagatgat aaatatggtt    2140
aatttc                                                               2146
```

<210> SEQ ID NO 4
<211> LENGTH: 497
<212> TYPE: PRT
<213> ORGANISM: Homo sapiens

<400> SEQUENCE: 4

```
Met Thr Val Phe Leu Ser Phe Ala Phe Leu Ala Ala Ile Leu Thr His
  1               5                  10                  15

Ile Gly Cys Ser Asn Gln Arg Arg Ser Pro Glu Asn Ser Gly Arg Arg
                 20                  25                  30

Tyr Asn Arg Ile Gln His Gly Gln Cys Ala Tyr Thr Phe Ile Leu Pro
             35                  40                  45

Glu His Asp Gly Asn Cys Arg Glu Ser Thr Thr Asp Gln Tyr Asn Thr
         50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Val Leu Leu Lys
            260                 265                 270

Gly Gly Lys Arg Glu Glu Asp Lys Pro Phe Arg Asp Cys Ala Asp Val
        275                 280                 285

Tyr Gln Ala Gly Phe Asn Lys Ser Gly Ile Tyr Thr Ile Tyr Ile Asn
    290                 295                 300

Asn Met Pro Glu Pro Lys Lys Val Phe Cys Asn Met Asp Val Asn Gly
305                 310                 315                 320
```

-continued

Gly Gly Trp Thr Val Ile Gln His Arg Glu Asp Gly Ser Leu Asp Phe
            325                 330                 335

Gln Arg Gly Trp Lys Glu Tyr Lys Met Gly Phe Gly Asn Pro Ser Gly
            340                 345                 350

Glu Tyr Trp Leu Gly Asn Glu Phe Ile Phe Ala Ile Thr Ser Gln Arg
            355                 360                 365

Gln Tyr Met Leu Arg Ile Glu Leu Met Asp Trp Glu Gly Asn Arg Ala
        370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
            405                 410                 415

Leu Ile Leu His Gly Ala Asp Phe Ser Thr Lys Asp Ala Asp Asn Asp
            420                 425                 430

Asn Cys Met Cys Lys Cys Ala Leu Met Leu Thr Gly Gly Trp Trp Phe
            435                 440                 445

Asp Ala Cys Gly Pro Ser Asn Leu Asn Gly Met Phe Tyr Thr Ala Gly
        450                 455                 460

Gln Asn His Gly Lys Leu Asn Gly Ile Lys Trp His Tyr Phe Lys Gly
465                 470                 475                 480

Pro Ser Tyr Ser Leu Arg Ser Thr Thr Met Met Ile Arg Pro Leu Asp
            485                 490                 495

Phe

<210> SEQ ID NO 5
<211> LENGTH: 2282
<212> TYPE: DNA
<213> ORGANISM: Homo sapiens
<220> FEATURE:
<221> NAME/KEY: CDS
<222> LOCATION: (357)..(1844)

<400> SEQUENCE: 5
gaattcctgg gttggtgttt atctcctccc agccttgagg gagggaacaa cactgtagga      60
tctggggaga gaggaacaaa ggaccgtgaa agctgctctg taaaagctga cacagccctc     120
ccaagtgagc aggactgttc ttcccactgc aatctgacag tttactgcat gcctggagag     180
aacacagcag taaaaccag gtttgctact ggaaaaagag gaaagagaag actttcattg      240
acggacccag ccatggcagc gtagcagccc tgcgtttcag acggcagcag ctcgggactc     300
tggacgtgtg tttgccctca gtttgctaa gctgctggtt tattactgaa gaaaga atg     359
                                                                Met
                                                                  1 tgg cag att gtt ttc ttt act ctg agc tgt gat ctt gtc ttg gcc gca     407
Trp Gln Ile Val Phe Phe Thr Leu Ser Cys Asp Leu Val Leu Ala Ala
            5                  10                  15 gcc tat aac aac ttt cgg aag agc atg gac agc ata gga aag aag caa     455
Ala Tyr Asn Asn Phe Arg Lys Ser Met Asp Ser Ile Gly Lys Lys Gln
        20                  25                  30 tat cag gtc cag cat ggg tcc tgc agc tac act ttc ctc ctg cca gag     503
Tyr Gln Val Gln His Gly Ser Cys Ser Tyr Thr Phe Leu Leu Pro Glu
    35                  40                  45 atg gac aac tgc cgc tct tcc tcc agc ccc tac gtg tcc aat gct gtg     551
Met Asp Asn Cys Arg Ser Ser Ser Ser Pro Tyr Val Ser Asn Ala Val
50                  55                  60                  65 cag agg gac gcg ccg ctc gaa tac gat gac tcg gtg cag agg ctg caa     599
Gln Arg Asp Ala Pro Leu Glu Tyr Asp Asp Ser Val Gln Arg Leu Gln
            70                  75                  80

| | | |
|---|---|---|
| gtg ctg gag aac atc atg gaa aac aac act cag tgg cta atg aag ctt<br>Val Leu Glu Asn Ile Met Glu Asn Asn Thr Gln Trp Leu Met Lys Leu<br>              85                          90                          95 | 647 | |
| gag aat tat atc cag gac aac atg aag aaa gaa atg gta gag ata cag<br>Glu Asn Tyr Ile Gln Asp Asn Met Lys Lys Glu Met Val Glu Ile Gln<br>            100                        105                      110 | 695 | |
| cag aat gca gta cag aac cag acg gct gtg atg ata gaa ata ggg aca<br>Gln Asn Ala Val Gln Asn Gln Thr Ala Val Met Ile Glu Ile Gly Thr<br>115                          120                      125 | 743 | |
| aac ctg ttg aac caa aca gct gag caa acg cgg aag tta act gat gtg<br>Asn Leu Leu Asn Gln Thr Ala Glu Gln Thr Arg Lys Leu Thr Asp Val<br>130                          135                      140                      145 | 791 | |
| gaa gcc caa gta tta aat cag acc acg aga ctt gaa ctt cag ctc ttg<br>Glu Ala Gln Val Leu Asn Gln Thr Thr Arg Leu Glu Leu Gln Leu Leu<br>                          150                      155                      160 | 839 | |
| gaa cac tcc ctc tcg aca aac aaa ttg gaa aaa cag att ttg gac cag<br>Glu His Ser Leu Ser Thr Asn Lys Leu Glu Lys Gln Ile Leu Asp Gln<br>                165                      170                      175 | 887 | |
| acc agt gaa ata aac aaa ttg caa gat aag aac agt ttc cta gaa aag<br>Thr Ser Glu Ile Asn Lys Leu Gln Asp Lys Asn Ser Phe Leu Glu Lys<br>            180                        185                      190 | 935 | |
| aag gtg cta gct atg gaa gac aag cac atc atc caa cta cag tca ata<br>Lys Val Leu Ala Met Glu Asp Lys His Ile Ile Gln Leu Gln Ser Ile<br>195                          200                      205 | 983 | |
| aaa gaa gag aaa gat cag cta cag gtg tta gta tcc aag caa aat tcc<br>Lys Glu Glu Lys Asp Gln Leu Gln Val Leu Val Ser Lys Gln Asn Ser<br>210                          215                      220                      225 | 1031 | |
| atc att gaa gaa cta gaa aaa aaa ata gtg act gcc acg gtg aat aat<br>Ile Ile Glu Glu Leu Glu Lys Lys Ile Val Thr Ala Thr Val Asn Asn<br>                          230                      235                      240 | 1079 | |
| tca gtt ctt caa aag cag caa cat gat ctc atg gag aca gtt aat aac<br>Ser Val Leu Gln Lys Gln Gln His Asp Leu Met Glu Thr Val Asn Asn<br>                245                      250                      255 | 1127 | |
| tta ctg act atg atg tcc aca tca aac tca gct aag gac ccc act gtt<br>Leu Leu Thr Met Met Ser Thr Ser Asn Ser Ala Lys Asp Pro Thr Val<br>            260                        265                      270 | 1175 | |
| gct aaa gaa gaa caa atc agc ttc aga gac tgt gct gaa gta ttc aaa<br>Ala Lys Glu Glu Gln Ile Ser Phe Arg Asp Cys Ala Glu Val Phe Lys<br>275                          280                      285 | 1223 | |
| tca gga cac acc aca aat ggc atc tac acg tta aca ttc cct aat tct<br>Ser Gly His Thr Thr Asn Gly Ile Tyr Thr Leu Thr Phe Pro Asn Ser<br>290                          295                      300                      305 | 1271 | |
| aca gaa gag atc aag gcc tac tgt gac atg gaa gct gga gga gcc ggg<br>Thr Glu Glu Ile Lys Ala Tyr Cys Asp Met Glu Ala Gly Gly Gly Gly<br>                          310                      315                      320 | 1319 | |
| tgg aca att att cag cga cgt gag gat ggc agc gtt gat ttt cag agg<br>Trp Thr Ile Ile Gln Arg Arg Glu Asp Gly Ser Val Asp Phe Gln Arg<br>                          325                      330                      335 | 1367 | |
| act tgg aaa gaa tat aaa gtg gga ttt ggt aac cct tca gga gaa tat<br>Thr Trp Lys Glu Tyr Lys Val Gly Phe Gly Asn Pro Ser Gly Glu Tyr<br>            340                        345                      350 | 1415 | |
| tgg ctg gga aat gag ttt gtt tcg caa ctg act aat cag caa cgc tat<br>Trp Leu Gly Asn Glu Phe Val Ser Gln Leu Thr Asn Gln Gln Arg Tyr<br>355                          360                      365 | 1463 | |
| gtg ctt aaa ata cac ctt aaa gac tgg gaa ggg aat gag gct tac tca<br>Val Leu Lys Ile His Leu Lys Asp Trp Glu Gly Asn Glu Ala Tyr Ser<br>370                          375                      380                      385 | 1511 | |
| ttg tat gaa cat ttc tat ctc tca agt gaa gaa ctc aat tat agg att<br>Leu Tyr Glu His Phe Tyr Leu Ser Ser Glu Glu Leu Asn Tyr Arg Ile | 1559 | |

-continued

```
                390                  395                   400
cac ctt aaa gga ctt aca ggg aca gcc ggc aaa ata agc agc atc agc        1607
His Leu Lys Gly Leu Thr Gly Thr Ala Gly Lys Ile Ser Ser Ile Ser
            405                 410                 415 caa cca gga aat gat ttt agc aca aag gat gga gac aac gac aaa tgt        1655
Gln Pro Gly Asn Asp Phe Ser Thr Lys Asp Gly Asp Asn Asp Lys Cys
        420                 425                 430 att tgc aaa tgt tca caa atg cta aca gga ggc tgg tgg ttt gat gca        1703
Ile Cys Lys Cys Ser Gln Met Leu Thr Gly Gly Trp Trp Phe Asp Ala
435                 440                 445 tgt ggt cct tcc aac ttg aac gga atg tac tat cca cag agg cag aac        1751
Cys Gly Pro Ser Asn Leu Asn Gly Met Tyr Tyr Pro Gln Arg Gln Asn
450                 455                 460                 465 aca aat aag ttc aac ggc att aaa tgg tac tac tgg aaa ggc tca ggc        1799
Thr Asn Lys Phe Asn Gly Ile Lys Trp Tyr Tyr Trp Lys Gly Ser Gly
                470                 475                 480 tat tcg ctc aag gcc aca acc atg atg atc cga cca gca gat ttc            1844
Tyr Ser Leu Lys Ala Thr Thr Met Met Ile Arg Pro Ala Asp Phe
            485                 490                 495 taaacatccc agtccacctg aggaactgtc tcgaactatt ttcaaagact taagcccagt      1904
gcactgaaag tcacggctgc gcactgtgtc ctcttccacc acagagggcg tgtgctcggt      1964
gctgacggga cccacatgct ccagattaga gcctgtaaac tttatcactt aaacttgcat      2024
cacttaacgg accaaagcaa gaccctaaac atccataatt gtgattagac agaacccta      2084 tgcaaagatg aacccgaggc tgagaatcag actgacagtt tacagacgct gctgtcacaa      2144
ccaagaatgt tatgtgcaag tttatcagta ataactgga aaacagaaca cttatgttat       2204
acaatacaga tcatcttgga actgcattct tctgagcact gtttatacac tgtgtaaata      2264
cccatatgtc ctgaattc                                                    2282

<210> SEQ ID NO 6
<211> LENGTH: 496
<212> TYPE: PRT
<213> ORGANISM: Homo sapiens

<400> SEQUENCE: 6

Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Ser Pro Tyr Val Ser Asn Ala
        50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160
```

```
Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
                180                 185                 190

Lys Lys Val Leu Ala Met Glu Asp Lys His Ile Ile Gln Leu Gln Ser
                195                 200                 205

Ile Lys Glu Glu Lys Asp Gln Leu Gln Val Leu Val Ser Lys Gln Asn
                210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
                275                 280                 285

Lys Ser Gly His Thr Thr Asn Gly Ile Tyr Thr Leu Thr Phe Pro Asn
                290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
                340                 345                 350

Tyr Trp Leu Gly Asn Glu Phe Val Ser Gln Leu Thr Asn Gln Gln Arg
                355                 360                 365

Tyr Val Leu Lys Ile His Leu Lys Asp Trp Glu Gly Asn Glu Ala Tyr
                370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
                435                 440                 445

Ala Cys Gly Pro Ser Asn Leu Asn Gly Met Tyr Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```

NUCLEIC ACID ENCODING TIE-2 LIGAND

CROSS-REFERENCE TO RELATED APPLICATIONS

This Application is a divisional of application Ser. No. 09/442,717 filed Nov. 18, 1999, now U.S. Pat. No. 6,627,415, which is a continuation of application Ser. No. 08/930,721 filed Mar. 10, 1998, now abandoned, which is the National Stage of International Application No. PCT/US96/04806 filed Apr. 5, 1996, which claims priority to International Application No. PCT/US95/12935 filed Oct. 6, 1995, and U.S. application Ser. No. 08/418,595 filed Apr. 6, 1995, now U.S. Pat. No. 5,814,464, the contents of each of which are hereby incorporated by reference.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to novel ligands, known as the TIE-2 ligands, that bind the TIE-2 receptor, as well as to methods of making and using the TIE-2 ligands. The invention further provides nucleic acid sequences encoding TIE-2 ligands, and methods for the generation of nucleic acids encoding TIE-2 ligands and their gene products. The TIE-2 ligands, as well as nucleic acids encoding them, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. In addition, the ligands may be used to promote the proliferation and/or differentiation of hematopoietic stem cells.

More generally, biologically active TIE-2 ligands may be used to promote the growth, survival, migration, and/or differentiation and/or stabilization or destabilization of cells expressing the TIE-2 receptor. Biologically active TIE-2 ligand may be used for the in vitro maintenance of TIE-2 receptor expressing cells in culture. Cells and tissues expressing TIE-2 receptor include, for example, cardiac and vascular endothelial cells, lens epithelium and heart epicardium and early hematopoietic cells. Alternatively, such ligand may be used to support cells which are engineered to express TIE-2 receptor. Further, TIE-2 ligands and their cognate receptor may be used in assay systems to identify agonists or antagonists of the TIE-2 receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosine residues in proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass 1) and insulin receptor-like kinase (subclass 11), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "TIE" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. Specifically, tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus the TIEs has been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene, which, like tie, has been reported to be expressed in the mouse exclusively in endothelial cells and their presumptive progenitors. Dumont, et al. Oncogene 8: 1293–1301 (1993). The human homolog of tie-2 is described in Ziegler, U.S. Pat. No. 5,447,860 which issued on Sep. 5, 1995 (wherein it is referred to as "ork"), which is incorporated in its entirety herein.

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that the TIEs plays a role in the development and maintenance of the vascular system. This could include roles in endothelial cell determination, proliferation, differentiation and cell migration and patterning into vascular elements. Analyses of mouse embryos deficient in TIE-2 illustrate its importance in angiogenesis, particularly for vascular network formation in endothelial cells. Sato, T. N., et al., Nature 376:70–74 (1995). In the mature vascular system, the TIEs could function in endothelial cell survival, maintenance and response to pathogenic influences.

The TIE receptors are also expressed in primitive hematopoietic stem cells, B cells and a subset of megakaryocytic cells, thus suggesting the role of ligands which bind these receptors in early hematopoiesis, in the differentiation and/ or proliferation of B cells, and in the megakaryocytic differentiation pathway. Iwama, et al. Biochem. Biophys. Research Communications 195:301–309 (1993); Hashiyama, et al. Blood 87:93–101 (1996), Batard, et al. Blood 87:2212–2220 (1996).

SUMMARY OF THE INVENTION

The present invention provides for a composition comprising a TIE-2 ligand substantially free of other proteins. The invention also provides for an isolated nucleic acid molecule encoding a TIE-2 ligand. The isolated nucleic acid may be DNA, cDNA or RNA. The invention also provides for a vector comprising an isolated nucleic acid molecule encoding a TIE-2 ligand. The invention further provides for a host-vector system for the production in a suitable host cell of a polypeptide having the biological activity of a TIE-2 ligand. The suitable host cell may be bacterial, yeast, insect or mammalian. The invention also provides for a method of producing a polypeptide having the biological activity of a TIE-2 ligand which comprises growing cells of the host-vector system under conditions permitting production of the polypeptide and recovering the polypeptide so produced.

The invention herein described of an isolated nucleic acid molecule encoding a TIE-2 ligand further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds a TIE-2 ligand. The antibody may be monoclonal or polyclonal. Thus the invention further provides for therapeutic compositions comprising an antibody which specifically binds a TIE-2 ligand in a pharmaceutically acceptable vehicle. The invention also provides for a method of blocking blood vessel growth in a mammal by administering an effective amount of a therapeutic composition comprising an antibody which specifically binds a TIE-2 ligand in a pharmaceutically acceptable vehicle.

The invention further provides for therapeutic compositions comprising a TIE-2 ligand in a pharmaceutically acceptable vehicle. The invention also provides for a method of promoting neovascularization in a patient by administering an effective amount of a therapeutic composition comprising a TIE-2 ligand in a pharmaceutically acceptable vehicle. In one embodiment, the method may be used to promote wound healing. In another embodiment, the method may be used to treat ischemia. In yet another embodiment, a TIE-2 ligand is used, alone or in combination with other hematopoietic factors, to promote the proliferation or differentiation of hematopoietic stem cells, B cells or megakaryocytic cells.

Alternatively, the invention provides that a TIE-2 ligand may be conjugated to a cytotoxic agent and a therapeutic composition prepared therefrom. The invention further provides for a receptorbody which specifically binds a TIE-2 ligand. The invention further provides for therapeutic compositions comprising a receptorbody which specifically binds a TIE-2 ligand in a pharmaceutically acceptable vehicle. The invention also provides for a method of blocking blood vessel growth in a mammal by administering an effective amount of a therapeutic composition comprising a receptorbody which specifically binds a TIE-2 ligand in a pharmaceutically acceptable vehicle.

The invention also provides for a TIE-2 receptor antagonist as well as a method of inhibiting TIE-2 ligand biological activity in a mammal comprising administering to the mammal an effective amount of a TIE-2 antagonist. According to the invention, the antagonist may be the TIE-2 ligand 2 as described herein, an antibody or other molecule capable of specifically binding either TIE-2 ligand 1 or TIE-2 receptor (such as for example TIE-2 receptorbody), or ligandbody comprising the fibrinogen-like domain of TIE-2 ligand 1 or ligand 2.

BRIEF DESCRIPTION OF THE FIGURES

FIG. 1A: embryos treated with EHK-1 RB (rEHK-1 ecto/hIgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

FIG. 4A-4F—Nucleic acid and deduced amino acid (single letter code) sequences of human TIE-2 ligand 1 from clone λgt10 encoding htie-2 ligand 1 (SEQ ID NO:1 and SEQ ID NO:2).

FIG. 5A-5F—Nucleic acid and deduced amino acid (single letter code) sequences of human TIE-2 ligand 2 ligand 1 from T98G clone (SEQ ID NO:3 and SEQ ID NO:4).

FIG. 6A-6F—Nucleic acid and deduced amino acid (single letter code) sequences of human TIE-2 ligand 2 from clone pBluescript KS encoding human TIE 2 ligand 2 (SEQ ID NO:5 and SEQ ID NO:6).

FIG. 11—Binding of recombinant human TIE-2 ligand 1 (hTL1) and human TIE-2 ligand 2 (hTL2), in COS cell supernatants, to a human TIE-2 receptorbody (RB) immobilized surface. Human TIE-2-specific binding was determined by incubating the samples with 25 μg/ml of either soluble human TIE-2 RB or trkB RB; significant reduction in the binding activity is observed only for the samples incubated with human TIE-2 RB.

FIG. 19—A typical curve of TIE-2-IgG binding to immobilized TL1 in a quantitative cell-free binding assay.

FIG. 20—A typical curve showing TIE-2 ligand 1 ligandbody comprising the fibrinogen-like domain of the ligand bound to the Fc domain of IgG (TL1-fFc) binding to immobilized TIE-2 ectodomain in a quantitative cell-free binding assay.

DETAILED DESCRIPTION OF THE INVENTION

Figure 1A:
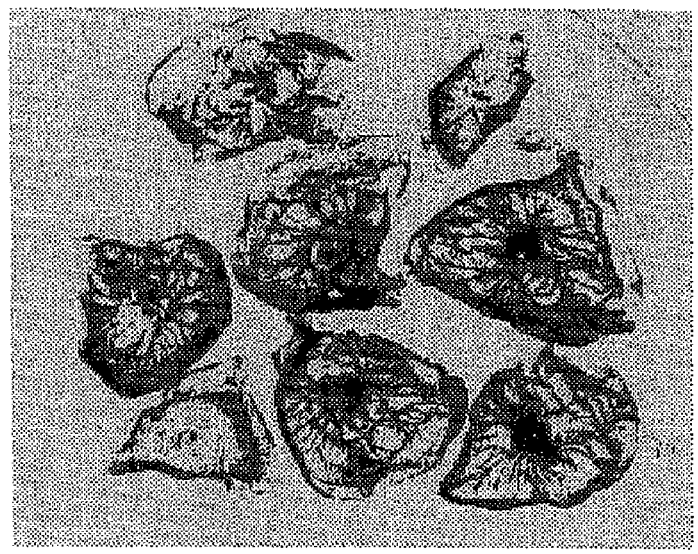
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 μg of RB was inserted immediately under the CAM of 1-day chick embryos. After 3 further days of incubation, 4 day old embryos and surrounding CAM were removed and examined.

As described in greater detail below, applicants have isolated and identified novel ligands that bind the TIE-2 receptor. The TTE-2 ligands of the present invention, which may be purified from nature, or made recombinantly, are referred to herein as TIE-2 ligand 1 (or TL1) and TIE-2 ligand 2 (or TL2). TIE-2 ligand 1, which has an amino acid sequence which is encoded, inter alia, by the nucleic acid set forth in FIG. 4A-4F (SEQ ID NO:1) or FIG. 5A-5F (SEQ ID NO:3), is a TIE-2 receptor agonist. TIE-2 ligand 2, which has an amino acid sequence which is encoded, inter alia, by the nucleic acid described in FIG. 6A-6F (SEQ ID NO:5), is a TIE-2 receptor antagonist.

The present invention comprises these TIE-2 ligands, as defined by their amino acid sequences, as well as functionally equivalent variants thereof comprising naturally occurring allelic variations, as well as proteins or peptides comprising substitutions, deletions or insertional mutants of the described sequences, which bind the TIE-2 receptors and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Also included within the scope of the invention are proteins or fragments or derivatives thereof which exhibit the same or similar biological activity as the TIE-2 ligands described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g. *E. coli*) expression systems. Functional equivalents also include mutants in which amino acid substitutions are made for cysteine molecules to improve stability of the molecules and to prevent unwanted crosslinking. As used herein, the term "TIE-2 ligand" also include fragments of the TIE-2 ligands which are associated with the binding of the ligands to the TIE-2 receptor. In a preferred embodiment, the TIE-2 ligand comprises the fibrinogen-like domain of TIE-2 ligands 1 and 2 as described herein.

The present invention also encompasses the nucleotide sequence that encodes the proteins described herein as TIE-2 ligands 1 and 2, as well as host cells, including yeast, bacteria, viruses, and mammalian cells, which are genetically engineered to produce the protein, by transfection, transduction, infection, electroporation, or microinjection of nucleic acid encoding the TIE-2 ligands described herein in a suitable expression vector. The present invention also encompasses introduction of the nucleic acids encoding TIE-2 ligands through gene therapy techniques such as is described, for example, in Finkel and Epstein FASEB J. 9:843–851 (1995); Guzman, et al. PNAS (USA) 91:10732–10736 (1994).

One skilled in the art will also recognize that the present invention encompasses DNA and RNA sequences that hybridize to a deduced TIE-2 ligand encoding sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a sequence deduced from an amino acid sequence of a TIE-2 ligand prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds the TIE-2 receptor and which has an amino acid sequence and other primary, secondary and tertiary characteristics that are sufficiently duplicative of the ligands described herein so as to confer on the molecule the same biological activity as one of the TIE-2 ligands described herein.

Accordingly, the present invention encompasses an isolated and purified nucleic acid molecule comprising a nucleic acid sequence encoding a human TIE-2 ligand, wherein the nucleic acid sequence is selected from the group consisting of:
(a) the nucleic acid sequence comprising the coding region of the human TIE-2 ligand as set forth in FIG. 4A-4F (SEQ ID NO:1), FIG. 5A-5F (SEQ ID NO:3) or FIG. 6A-6F (SEQ ID NO:5);
(b) a nucleic acid sequence that hybridizes under moderately stringent conditions to the nucleic acid sequence of (a) and which encodes a TIE-2 ligand that binds TIE-2 receptor; and
(c) a nucleic acid sequence that is degenerate as a result of the genetic code to a nucleic acid sequence of (a) or (b), and which encodes a TIE-2 ligand that binds TIE-2 receptor.

The present invention further provides for an isolated and purified human TIE-2 ligand encoded by an isolated nucleic acid molecule of the invention. The invention also provides a vector which comprises an isolated nucleic acid molecule comprising a nucleic acid sequence encoding a human TIE-2 ligand. In one embodiment, the vector is designated as pBluescript KS encoding human TIE 2 ligand 2.

Any of the methods known to one skilled in the art for the insertion of DNA fragments into a vector may be used to construct expression vectors encoding TIE-2 ligands using appropriate transcriptional/translational control signals and the protein coding sequences. These methods may include in vitro recombinant DNA and synthetic techniques and in vivo recombinations (genetic recombination). Expression of a nucleic acid sequence encoding a TIE-2 ligand or peptide fragments thereof may be regulated by a second nucleic acid sequence which is operably linked to the TIE-2 ligand encoding sequence such that the TIE-2 ligand protein or peptide is expressed in a host transformed with the recombinant DNA molecule. For example, expression of a TIE-2 ligand described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MuLV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the metallothionein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the tac promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals; elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells [Hanahan, Nature 315:115–122 (1985)]; immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315: 338–340; Kollias et al., 1986, Cell 46:89–94); myelin basic protein gene control region which is active in oligodendrocytes in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding a TIE-2 ligand to modulate its expression. Ecker, U.S. Pat. No. 5,166,195, issued Nov. 24, 1992.

Thus, according to the invention, expression vectors capable of being replicated in a bacterial or eukaryotic host comprising a nucleic acid encoding a TIE-2 ligand as described herein, are used to transfect a host and thereby direct expression of such nucleic acid to produce the TIE-2 ligand, which may then be recovered in a biologically active form. As used herein, a biologically active form includes a form capable of binding to the TIE-2 receptor and causing a biological response such as a differentiated function or influencing the phenotype of the cell expressing the receptor. Such biologically active forms would, for example, induce phosphorylation of the tyrosine kinase domain of the TIE-2 receptor. Alternatively, the biological activity may be an effect as an antagonist to the TIE-2 receptor, such as is the biological activity of TIE-2 ligand 2. In alternative embodiments, the active form of a TIE-2 ligand is one that can recognize the TIE-2 receptor and thereby act as a targeting agent for the receptor for use in both diagnostics and therapeutics. In accordance with such embodiments, the active form need not confer upon any TIE-2 expressing cell any change in phenotype.

In an alternative embodiment, the biologically active form of the TIE-2 ligand is one in which the ligand is capable of binding the TIE-1 receptor. Preliminary data indicates that TL 2 binds TIE-1 receptor (albeit with low affinity) raising the possibility that it may be able to bind and activate the receptor, or, as in the case of the TIE-2 receptor, bind and act as antagonist.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE-2 ligand encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a TIE-2 ligand gene product, for example, by binding of the ligand to the TIE-2 receptor or portion thereof which may be tagged with, for example, a detectable antibody or portion thereof or by binding to antibodies produced against the TIE-2 ligand protein or a portion thereof. Cells of the present invention may transiently or, preferably, constitutively and permanently express TIE-2 ligands as described herein. In the fourth approach, DNA nucleotide primers can be prepared corresponding to a tie-2 specific DNA sequence. These primers could then be used to PCR a tie-2 gene fragment. (PCR Protocols: A Guide To Methods and Applications, Edited by Michael A. Innis et al., Academic Press (1990)).

The recombinant ligands may be purified by any technique which allows for the subsequent formation of a stable, biologically active protein. Preferably, the ligands are secreted into the culture medium from which they are recovered. Alternatively, the ligand may be recovered from cells either as soluble proteins or as inclusion bodies, from which they may be extracted quantitatively by 8M guanidinium hydrochloride and dialysis in accordance with well known methodology. In order to further purify the ligand, affinity chromatography, conventional ion exchange chromatography, hydrophobic interaction chromatography, reverse phase chromatography or gel filtration may be used.

In additional embodiments of the invention, as described in greater detail in the Examples, a recombinant TIE-2 ligand encoding gene may be used to inactivate or "knock out" the endogenous gene by homologous recombination, and thereby create a TIE-2 ligand deficient cell, tissue, or animal. For example, and not by way of limitation, the recombinant TIE-2 ligand encoding gene may be engineered to contain an insertional mutation, for example the neo gene, which would inactivate the native TIE-2 ligand encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE-2 ligand encoding gene may then be identified, e.g. by Southern blotting, PCR detection, Northern blotting or assay of expression. Cells lacking an intact TIE-2 ligand encoding gene may then be fused to early embryo cells to generate transgenic animals deficient in such ligand. Such an animal may be used to define specific in vivo processes, normally dependent upon the ligand.

The present invention also provides for antibodies to the TIE-2 ligands described herein which are useful for detection of the ligands in, for example, diagnostic applications. For preparation of monoclonal antibodies directed toward TIE-2 ligand, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the TIE-2 ligands described herein. For the production of antibody, various host animals, including but not limited to rabbits, mice and rats can be immunized by injection with a TIE-2 ligand, or a fragment or derivative thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected TIE-2 ligand epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of a TIE-2 ligand in a biological sample by
a) contacting the biological sample with at least one antibody which specifically binds the TIE-2 ligand so that the antibody forms a complex with any TIE-2 ligand present in the sample; and
b) measuring the amount of the complex and thereby measuring the amount of the TIE-2 ligand in the biological sample.

The invention further encompasses an assay for measuring the amount of TIE-2 receptor in a biological sample by
a) contacting the biological sample with at least one ligand of the invention so that the ligand forms a complex with the TIE-2 receptor; and
b) measuring the amount of the complex and thereby measuring the amount of the TIE-2 receptor in the biological sample.

The present invention also provides for the utilization of a TIE-2 ligand to support the survival and/or growth and/or migration and/or differentiation of TIE-2 receptor expressing cells. Thus, the ligand may be used as a supplement to support, for example, endothelial cells in culture.

Further, the discovery by applicants of a cognate ligand for the TIE-2 receptor enables the utilization of assay systems useful for the identification of agonists or antagonists of the TIE-2 receptor. Such assay systems would be useful in identifying molecules capable of promoting or inhibiting angiogenesis. For example, in one embodiment, antagonists of the TIE-2 receptor may be identified as test molecules that are capable of interfering with the interaction of the TIE-2 receptor with a biologically active TIE-2 ligand. Such antagonists are identified by their ability to 1) block the binding of a biologically active TIE-2 ligand to the receptor as measured, for example, using BIAcore biosensor technology (BIAcore; Pharmacia Biosensor, Piscataway, N.J.); or 2) block the ability of a biologically active TIE-2 ligand to cause a biological response. Such biological responses include, but are not limited to, phosphorylation of the TIE-2 receptor or downstream components of the TIE-2 signal transduction pathway, or survival, growth or differentiation of TIE-2 receptor bearing cells.

In one embodiment, cells engineered to express the TIE-2 receptor may be dependent for growth on the addition of TIE-2 ligand. Such cells provide useful assay systems for identifying additional agonists of the TIE-2 receptor, or antagonists capable of interfering with the activity of TIE-2 ligand on such cells. Alternatively, autocrine cells, engineered to be capable of co-expressing both TIE-2 ligand and receptor, may provide useful systems for assaying potential agonists or antagonists.

Therefore, the present invention provides for introduction of the TIE-2 receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of the TIE-2 receptor (or a chimeric receptor comprising the extracellular domain of another receptor tyrosine kinase such as, for example, trkC and the intracellular domain of a TIE receptor) into a fibroblast cell line (e.g., NIH3T3 cells) thus such a receptor which does not normally mediate proliferative or other responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express the TIE-2 ligands, thus creating an autocrine system useful for assaying for molecules that act as antagonists/agonists of this interaction. Thus, the present invention provides for host cells comprising nucleic acid encoding TIE-2 ligands and nucleic acid encoding TIE-2 receptor.

The TIE-2 receptor/TIE-2 ligand interaction also provides a useful system for identifying small molecule agonists or antagonists of the TIE-2 receptor. For example, fragments, mutants or derivatives of a TIE-2 ligand may be identified that bind the TIE-2 receptor but do not induce any other biological activity. Alternatively, the characterization of a TIE-2 ligand enables the determination of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to the TIE-2 receptor may be measured in a number of ways. For example, the actual binding of test molecule to cells expressing TIE-2 may be detected or measured, by detecting or measuring (i) test molecule bound to the surface of intact cells; (ii) test molecule cross-linked to TIE-2 protein in cell lysates; or (iii) test molecule bound to TIE-2 in vitro. The specific interaction between test molecule and TIE-2 may be evaluated by using reagents that demonstrate the unique properties of that interaction.

As a specific, nonlimiting example, the methods of the invention may be used as follows. Consider a case in which the TIE-2 ligand in a sample is to be measured. Varying dilutions of the sample (the test molecule), in parallel with a negative control (NC) containing no TIE-2 ligand activity, and a positive control (PC) containing a known amount of a TIE-2 ligand, may be exposed to cells that express TIE-2 in the presence of a detectably labeled TIE-2 ligand (in this example, radioiodinated ligand). The amount of TIE-2 ligand in the test sample may be evaluated by determining the amount of $^{125}$I-labeled TIE-2 ligand that binds to the controls and in each of the dilutions, and then comparing the sample values to a standard curve. The more TIE-2 ligand in the sample, the less $^{125}$I-ligand that will bind to TIE-2.

The amount of $^{125}$I-ligand bound may be determined by measuring the amount of radioactivity per cell, or by cross-linking the TIE-2 ligand to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE-2 receptor/TIE-2 ligand. The specific test molecule/TIE-2 interaction may further be tested by adding to the assays various dilutions of an unlabeled control ligand that does not bind the TIE-2 receptor and therefore should have no substantial affect on the competition between labeled TIE-2 ligand and test molecule for TIE-2 binding. Alternatively, a molecule known to be able to disrupt TIE-2 receptor/TIE-2 ligand binding, such as, but not limited to, anti-TIE-2 antibody, or TIE-2 receptorbody as described herein, may be expected to interfere with the competition between $^{125}$I-TIE-2 ligand and test molecule for TIE-2 receptor binding.

Detectably labeled TIE-2 ligand includes, but is not limited to, TIE-2 ligand linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

Alternatively, the specific binding of test molecule to TIE-2 may be measured by evaluating the secondary biological effects of TIE-2 ligand/TIE-2 receptor binding, including, but not limited to, cell growth and/or differentiation or immediate early gene expression or phosphorylation of TIE-2. For example, the ability of the test molecule to induce differentiation can be tested in cells that lack tie-2 and in comparable cells that express tie-2; differentiation in tie-2-expressing cells but not in comparable cells that lack tie-2 would be indicative of a specific test molecule/TIE-2 interaction. A similar analysis could be performed by detecting immediate early gene (e.g. fos and jun) induction in tie-2-minus and tie-2-plus cells, or by detecting phosphorylation of TIE-2 using standard phosphorylation assays known in the art. Such analysis might be useful in identifying agonists or antagonists that do not competitively bind to TIE-2.

Similarly, the present invention provides for a method of identifying an molecule that has the biological activity of a TIE-2 ligand comprising (i) exposing a cell that expresses tie-2 to a test molecule and (ii) detecting the specific binding of the test molecule to TIE-2 receptor, in which specific binding to TIE-2 positively correlates with TIE-2 like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-2-minus or engineered to be tie-2-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE ligand-like activity or identifying a molecule as having such activity comprising (i) exposing a test molecule to a TIE-2 receptor protein in vitro under conditions that permit binding to occur and (ii) detecting binding of the test molecule to the TIE-2 receptor protein, in which binding of test molecule to TIE-2 receptor correlates with TIE ligand-like activity. According to such methods, the TIE-2 receptor may or may not be substantially purified, may be affixed to a solid support (e.g. as an affinity column or as an ELISA assay), or may be incorporated into an artificial membrane. Binding of test molecule to TIE-2 receptor may be evaluated by any method known in the art. In preferred embodiments, the binding of test molecule may be detected or measured by evaluating its ability to compete with detectably labeled known TIE-2 ligands for TIE-2 receptor binding.

The present invention also provides for a method of detecting the ability of a test molecule to function as an antagonist of TIE ligand-like activity comprising detecting the ability of the molecule to inhibit an effect of TIE ligand binding to TIE-2 receptor on a cell that expresses the receptor. Such an antagonist may or may not interfere with TIE-2 receptor/TIE-2 ligand binding. Effects of TIE-2 ligand binding to TIE-2 receptor are preferably biological or biochemical effects, including, but not limited to, cell survival or proliferation, cell transformation, immediate early gene induction, or TIE-2 phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE-2 receptorbody may be bound to a solid support, such as a plastic multiwell plate. As a control, a known amount of TIE-2 ligand which has been Myc-tagged may then be introduced to the well and any tagged TIE ligand which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE-2 receptorbody or TIE-2 ligand or ligandbody is covalently attached to a solid support (e.g. carboxymethyl dextran on a gold surface), one of skill in the art would be able to determine if the blocker molecule is binding specifically to the ligand, ligandbody or to the receptorbody. To determine if the blocker molecule can neutralize the biological activity of the ligand, one of skill in the art could perform a phosphorylation assay (see Example 5) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE-2 receptor.

In addition, the invention further contemplates compositions wherein the TIE-2 ligand is the receptor binding domains of the TIE-2 ligands described herein. For example, TIE-2 ligand 1 consists of a "coiled coil" domain (beginning at the 5' end and extending to the nucleotide at about position 1160 of FIG. 4A-4F (SEQ ID NO:1) and about position 1157 of FIG. 5A-5F (SEQ ID NO:3)) and a fibrinogen-like domain (which is encoded by the nucleotide sequence of FIG. 4A-4F (SEQ ID NO:1) beginning at about position 1161 and about position 1158 of FIG. 5A-5F (SEQ ID NO:3)). The fibrinogen-like domain of TIE-2 ligand 2 is believed to begin on or around the same amino acid sequence as in ligand 1 (FRDCA) which is encoded by nucleotides beginning around 1197 of FIG. 6A-6F (SEQ ID NO:5). Multimerization of the coiled coil domains during production of the ligand hampers purification. As described in Example 19, Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti myc antibodies, do bind the TIE-2 receptor. [Methods of production of "clustered ligands and ligandbodies" are described in Davis, et al. Science 266:816–819 (1994)]. Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of TIE-2 ligandbodies which may be used as targeting agents, in diagnostics or in therapeutic applications, such as targeting agents for tumors, and/or associated vasculature wherein a TIE-2 antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE-2 receptor. Such molecules may be used in a method of treatment of the human or animal body, or in a method of diagnosis.

Because TIE-2 receptor has been identified in association with endothelial cells and, as demonstrated herein, blocking of TIE-2 ligand 1 appears to prevent vascularization, applicants have demonstrated that the TIE-2 ligand 1 will be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic. Ferrara, et al. U.S. Pat. No. 5,332,671 issued Jul. 26, 1994. The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. [see Sudo, et al. European Patent Application 0 550 296 A2 published Jul. 7, 1993; Banai, et al. Circulation 89:2183–2189 (1994); Unger, et al. Am. J. Physiol. 266: H1588–H1595 (1994); Lazarous, et al. Circulation 91:145–153 (1995)]. According to the invention, the TIE-2 ligands may be used alone or in combination with one or more additional pharmaceutically active compounds such as, for example, VEGF or basic fibroblast growth factor (bFGF), as well as cytokines, neurotrophins, etc.

Conversely, antagonists of the TIE-2 receptor, such as receptorbodies as described herein in Examples 2 and 3, and TIE-2 ligand 2 as described in Example 9, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. The TIE-2 ligands described herein may also be used in combination with agents, such as cytokine antagonists such as IL-6 antagonists, that are known to block inflammation.

For example, applicants have determined that the TIE-2 ligands are expressed in cells within, or closely associated with, tumors. TIE-2 ligand 2 appears to be tightly associated with tumor endothelial cells. Accordingly, TIE-2 antagonists, such as TIE-2 ligand 2 or TIE-2 ligandbodies may also be useful in preventing or attenuating, for example, tumor growth. In addition, TIE-2 ligands or ligandbodies may be useful for the delivery of toxins to a receptor bearing cell. Alternatively, other molecules, such as growth factors, cytokines or nutrients, may be delivered to a TIE-2 receptor bearing cell via TIE-2 ligands or ligandbodies. TIE-2 ligands or ligandbodies could also be used as a diagnostic reagent for the TIE-2 receptor, to detect the receptor in vivo or in vitro. Where the TIE-2 receptor is associated with a disease state, TIE-2 ligands or ligandbodies may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in Alitalo, et al. WO 95/26364 published Oct. 5, 1995 and Burrows, F. and P. Thorpe, PNAS (USA) 90:8996–9000 (1993) which is incorporated herein in its entirety.

In other embodiments, the TIE-2 ligands described herein are used as hematopoietic factors. A variety of hematopoietic factors and their receptors are involved in the proliferation and/or differentiation and/or migration of the various cells types contained within blood. Because the TIE-2 receptors are expressed in early hematopoietic cells, the TIE-2 ligands are expected to play a comparable role in the proliferation or differentiation or migration of these cells. Thus, for example, TIE-2 containing compositions may be prepared, assayed, examined in in vitro and in vivo biological systems and used therapeutically as described in any of the following: Sousa, U.S. Pat. No. 4,810,643, Lee, et al., Proc. Natl. Acad. Sci. USA 82:4360–4364 (1985) Wong, et al. Science, 228:810–814 (1985); Yokota, et al. Proc. Natl. Acad. Sci (USA) 81:1070 (1984); Bosselman, et al. WO 9105795 published May 2, 1991 entitled "Stem Cell Factor" and Kirkness, et al. WO 95/19985 published Jul. 27, 1995 entitled "Haemopoietic Maturation Factor". Accordingly, the ligands may be used to diagnose or treat conditions in which normal hematopoiesis is suppressed, including, but not limited to anemia, thrombocytopenia, leukopenia and granulocytopenia. In a preferred embodiment, the TIE-2 ligands may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The TIE-2 ligands of the present invention may be used alone, or in combination with another pharmaceutically active agent such as, for example, ctyokines, neurotrophins, interleukins, etc. In a preferred embodiment, the ligands may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE-2 receptor antagonists, such as TL2, are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the TIE-2 ligand 2, TIE-2 antibody, TIE-2 receptorbody, a conjugate of a TIE-2 ligand according to claim 27 or 28, or a ligandbody or fFC as described herein.

The present invention also provides for pharmaceutical compositions comprising the TIE-2 ligands or ligandbodies described herein, peptide fragments thereof, or derivatives in a pharmacologically acceptable vehicle. The TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a human TIE-2 ligand or ligandbody and a cytotoxic agent conjugated thereto. In one embodiment, the cytotoxic agent may be a radioisotope or toxin.

The invention also provides for an antibody which specifically binds a human TIE-2 ligand. The antibody may be monoclonal or polyclonal.

The invention further provides for a method of purifying a human TIE-2 ligand comprising:
  a) coupling at least one TIE-2 binding substrate to a solid matrix;
  b) incubating the substrate of a) with a cell lysate so that the substrate forms a complex with any human TIE-2 ligand in the cell lysate;
  c) washing the solid matrix; and
  d) eluting the human TIE-2 ligand from the coupled substrate.

The substrate may be any substance that specifically binds the human TIE-2 ligand. In one embodiment, the substrate is selected from the group consisting of anti-TIE-2 ligand antibody, TIE-2 receptor and TIE-2 receptorbody. The invention further provides for a receptorbody which specifically binds a human TIE-2 ligand, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising a human TIE-2 ligand or ligandbody in a pharmaceutically acceptable vehicle, as well as a method of promoting neovascularization in a patient comprising administering to the patient an effective amount of the therapeutic composition.

In addition, the present invention provides for a method for identifying a cell which expresses TIE-2 receptor which comprises contacting a cell with a detectably labeled TIE-2 ligand or ligandbody, under conditions permitting binding of the detectably labeled ligand to the TIE-2 receptor and determining whether the detectably labeled ligand is bound to the TIE-2 receptor, thereby identifying the cell as one which expresses TIE-2 receptor. The present invention also provides for a therapeutic composition comprising a TIE-2 ligand or ligandbody and a cytotoxic agent conjugated thereto. The cytotoxic agent may be a radioisotope or toxin.

The invention also provides a method of detecting expression of TIE-2 ligand by a cell which comprises obtaining mRNA from the cell, contacting the mRNA so obtained with a labeled nucleic acid molecule encoding a TIE-2 ligand, under hybridizing conditions, determining the presence of mRNA hybridized to the labeled molecule, and thereby detecting the expression of the TIE-2 ligand in the cell.

The invention further provides a method of detecting expression of a TIE-2 ligand in tissue sections which comprises contacting the tissue sections with a labeled nucleic acid molecule encoding a TIE-2 ligand, under hybridizing conditions, determining the presence of mRNA hybridized to the labelled molecule, and thereby detecting the expression of the TIE-2 ligand in tissue sections.

EXAMPLE 1

Identification of the ABAE Cell Line as Reporter Cells for the TIE-2 Receptor

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and, subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2\times10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at 14,000×G for 10 minutes, at 4° C. and the supernatants were subjected to immunoprecipitation with antisera specific for TIE-2 receptor, with or without the presence of blocking peptides added to ~20 μg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

EXAMPLE 2

Cloning and Expression of TIE-2 Receptorbody for Affinity-Based Study of TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-NotI fragment into the baculovirus transfer plasmid pVL1393. Plasmid DNA purified by cesium chloride density gradient centrifugation was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells ($2\times10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual.* 1992, New York: W. H. Freeman) except that the agarose overlay contained 125 μg/mL X-gal (5-bromo-4-chloro-3-indolyl-β-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 μg/mL MTT (3-[4,5-dimethylthiazol-2-yl]2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10$^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 µm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 receptorbody were pooled and dialyzed versus PBS.

EXAMPLE 3

Demonstration that TIE-2 has a Critical Role in Development of the Vasculature

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Figure 1B:
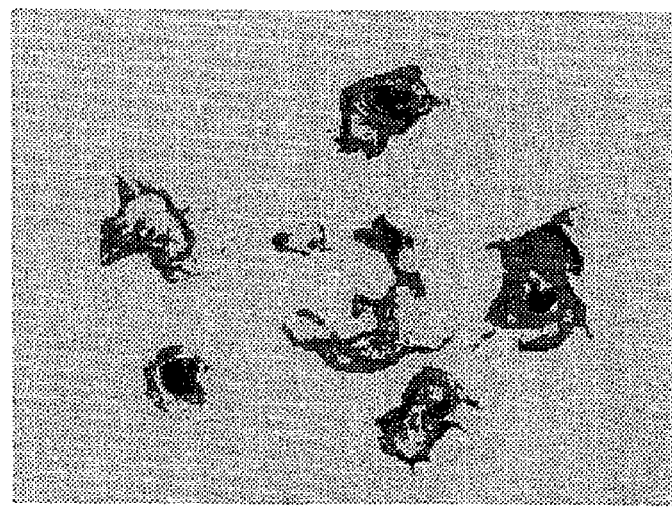

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 µg of protein in 30 µl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

Identification of a TIE-2-Specific Binding Activity in Conditioned Medium from the ras Oncogene-Transformed C2C12 Mouse Myoblast Cell Line Screening of ten-fold-concentrated cell-conditioned media (10×CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras), RAT 2-ras (which is a ras transformed fibroblast cell line), human glioblastoma T98G and the human neuroblastoma cell line known as SHEP-1.

The C2C12-ras 10×CCM originated from a stably transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10×CCM was made by plating the cells at 60% confluence in a serum free defined media for 12 hours. [Zhan and Goldfarb, Mol. Cell. Biol. 6: 3541–3544 (1986)); Zhan, et al. Oncogene 1: 369–376 (1987)]. The medium was discarded and replaced with fresh DMEM/Q/P-S for 24 hours. This medium was harvested and cells were re-fed fresh DMEM/Q/P-S, which was also harvested after a further 24 hours. These CCM were supplemented with the protease inhibitors PMSF (1 mM) and aprotinin (10 µg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10×CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). A negative control surface of the EHK-1 receptorbody was prepared in a similar manner.

The running buffer used in the system was HBS (10 mM Hepes, 3.4 mM EDTA, 150 mM NaCl, 0.005% P20 surfactant, pH 7.4). The 10×CCM samples were centrifuged for 15 min at 40° C. and further clarified using a sterile, low protein-binding 0.45 µm filter (Millipore; Bedford, Mass.). Dextran (2 mg/ml) and P20 surfactant (0.005%) were added to each CCM sample. Aliquots of 40 µL were injected across the immobilized surface (either TIE-2 or EHK-1) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-µL pulse of 3 M $MgCl_2$.

The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50× concentrated C2C12-ras CCM resulted in a four-fold enhancement over background of the TIE-2 specific binding signal.

EXAMPLE 5

C2C12-ras CCM Contains an Activity that Induces Tyrosine Phosphorylation of TIE-2 Receptor C2C12-ras 10×CCM was examined for its ability to induce tyrosine phosphorylation of TIE-2 in ABAE cells. Serum-starved ABAE cells were briefly incubated with C2C12-ras CCM, lysed and subjected to immunoprecipitation and Western analyses as described above. Stimulation of serum-starved ABAE cells with serum-free C2C12-ras 10×CCM was done as follows. The medium of ABAE cells starved as described above was removed and replaced with either defined medium or 10×CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100× increase in TIE-2 phosphorylation. This activity was almost totally depleted by pre-incubation of the C2C12-ras 10×CCM for 90 minutes at room temperature with 13 µg of TIE-2 RB coupled to protein G-Sepharose beads. Medium incubated with protein G Sepharose alone was not depleted of this phosphorylating activity.

EXAMPLE 6

Expression Cloning of TIE-2 Ligand

Figure 2:
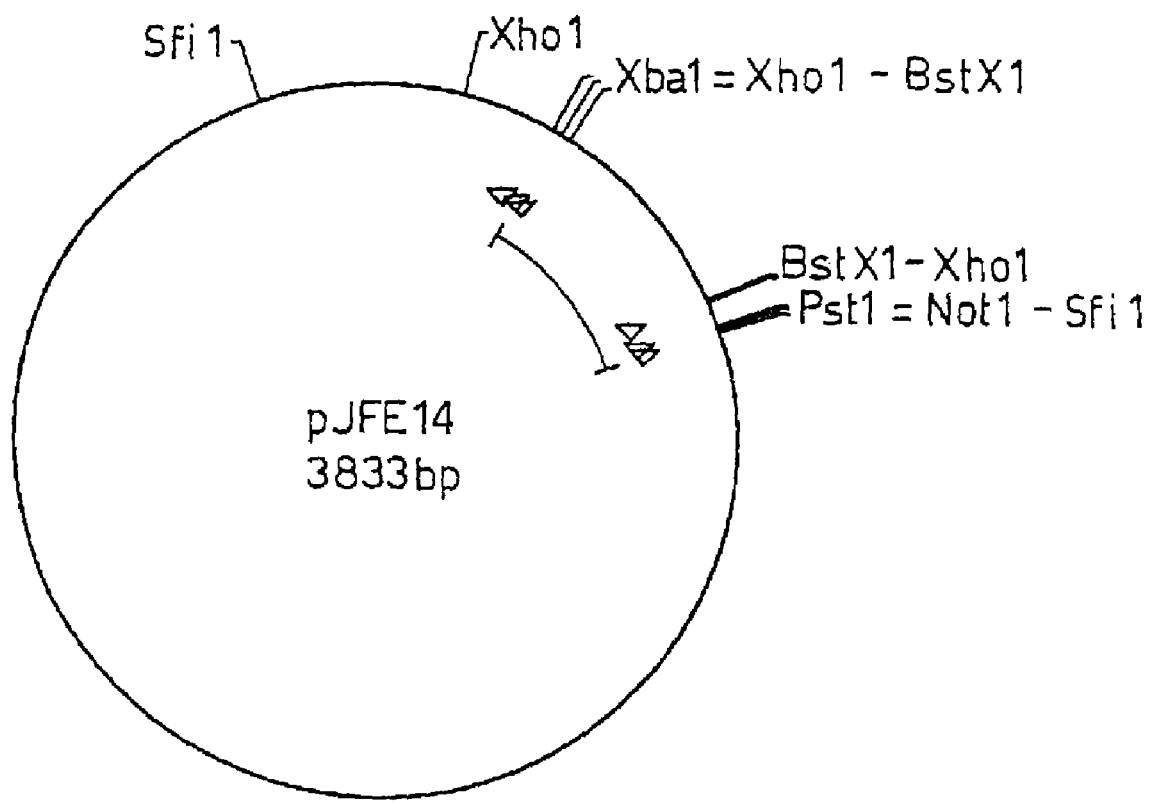
FIG. 2—Vector pJFE14.

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3–4 hours at 37° C. in an atmosphere of 5% $CO_2$. The transfection media was aspirated and replaced with PBS with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody (RB), which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2 RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

Isolation and Sequencing of Full Length cDNA Clone Encoding Human TIE-2 Ligand

Figure 3:
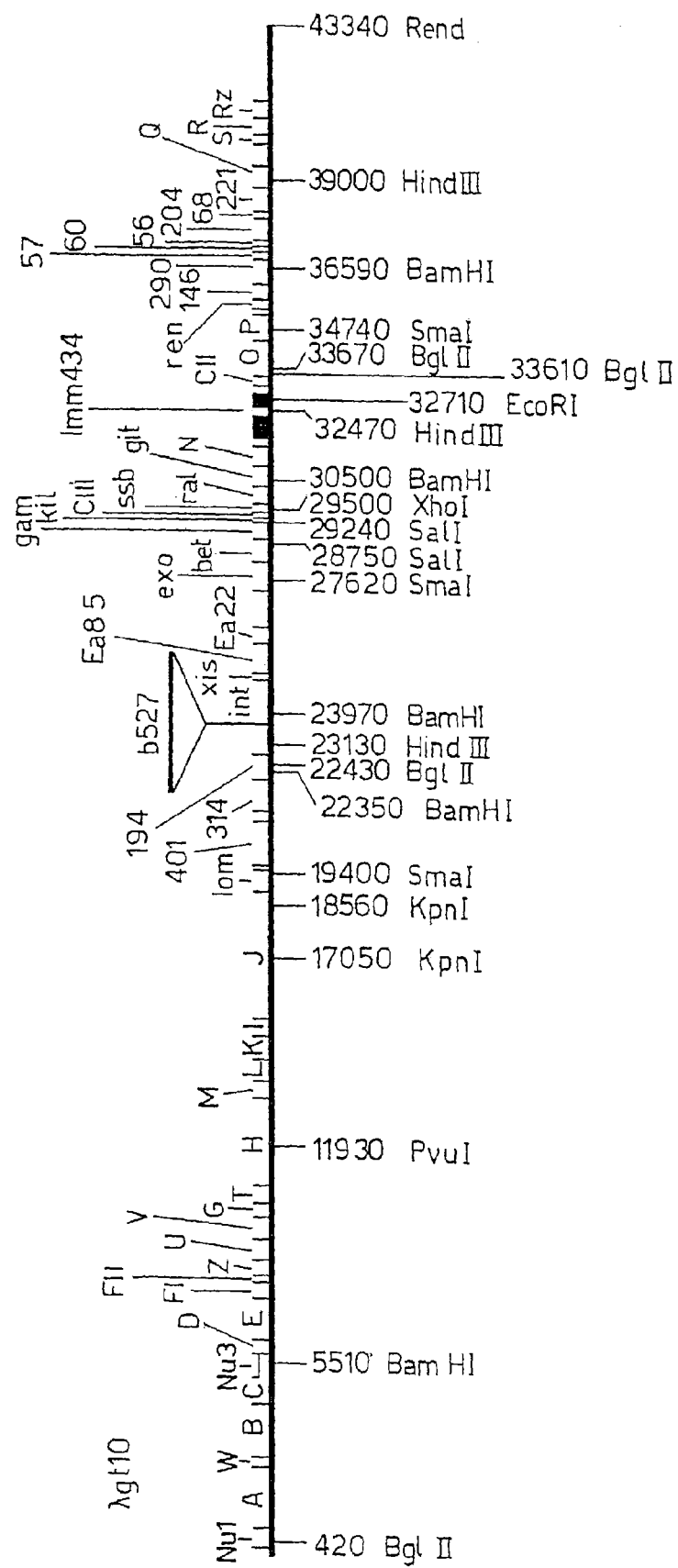
FIG. 3—Restriction map of λgt10.

A human fetal lung cDNA library in lambda gt-10 (see FIG. 3) was obtained from Clontech Laboratories, Inc. (Palo Alto, Calif.). Plaques were plated at a density of $1.25 \times 10^6/$ 20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5 \times 10^8$ cpm/ng. Hybridization was carried out at 65° C. in hybridization solution containing 0.5 mg/ml salmon sperm DNA. The filters were washed at 65° C. in 2×SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning of the human tie-2 ligand DNA into a mammalian expression vector may be accomplished as follows. The clone λgt10 encoding htie-2 ligand 1 contains an EcoRI site located 490 base pairs downstream from the start of the coding sequence for the human TIE-2 ligand. The coding region may be excised using unique restriction sites upstream and downstream of the initiator and stop codons respectively. For example, an SpeI site, located 70 bp 5' to the initiator codon, and a Bpu1102i (also known as BlpI) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpu1102i sites are both made blunt ended).

The coding region from the clone λgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone λgt10 encoding htie-2 ligand 1 is shown in FIG. 4A-4F (SEQ ID NO:1 and SEQ ID NO:2).

In addition, full length human tie-2 ligand cDNA clones were obtained by screening a human glioblastoma T98G cDNA library in the pJFE14 vector. Clones encoding human TIE-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone λgt10 encoding htie-2 ligand 1. As shown in FIG. 4A-4F (SEQ ID NO:1), the clone λgt10 encoding htie-2 ligand 1 contains an additional glycine residue which is encoded by nucleotides 1114–1116. The coding sequence of the T98G clone does not contain this glycine residue but otherwise is identical to the coding sequence of the clone λgt10 encoding htie-2 ligand 1. FIG. 5A-5F (SEQ ID NO:3 and SEQ ID NO:4) sets forth the nucleotide and deduced amino acid sequence of human TIE-2 ligand from the T98G clone.

EXAMPLE 8

Isolation and Sequencing of Second Full Length cDNA Clone A Encoding Human TIE-2 Ligand A human fetal lung cDNA library in lambda gt-10 (see FIG. 3) was obtained from Clontech Laboratories, Inc. (Palo Alto, Calif.). Plaques were plated at a density of $1.25 \times 10^6/$ 20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, New York). Duplicate filters were screened at low stringency (2×SSC, 55° C.) with probes made to the human TIE-2 ligand 1 sequence. One of the duplicate filters was probed with a 5' probe, encoding amino acids 25–265 of human TIE-2 ligand 1 as set forth in FIG. 4A-4F (SEQ ID NO:2). The second duplicate filter was probed with a 3' probe, encoding amino acids 282–498 of human TIE-2 ligand 1 sequence (see FIG. 4A-4F (SEQ ID NO:2)). Both probes were hybridized at 55° C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse TIE-2 ligand 1 (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells/100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2 receptorbody. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptorbody.

One of skill in the art will readily see that the described methods may be used to further identify other related members of the TIE ligand family.

The coding region from the clone pBluescript KS encoding human TIE-2 ligand 2 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE 2 ligand from the clone pBluescript KS encoding human TIE-2 ligand 2 is shown in FIG. 6A-6F (SEQ ID NO:5 and SEQ ID NO:6).

EXAMPLE 9

TIE-2 Ligand 2 is a Receptor Antagonist

Conditioned media from COS cells expressing either TIE-2 ligand 2 (TL2) or TIE-2 ligand 1 (TL1) were compared for their ability to activate TIE-2 receptors naturally present in human endothelial cell lines.

Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman, R. J., 1985, Proc. Natl. Acad. Sci. USA 82: 689–693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Figure 7:
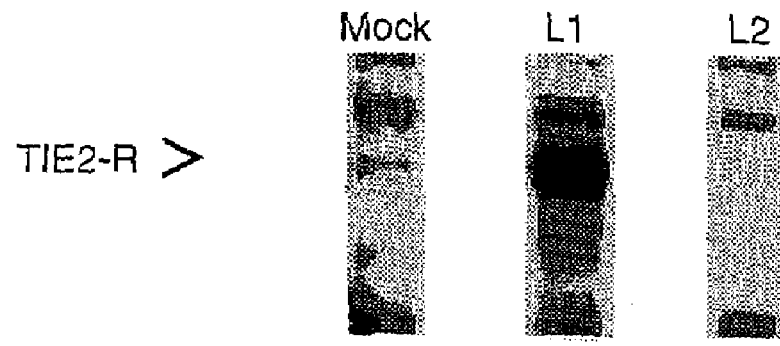
FIG. 7—Western blot showing activation of TIE-2 receptor by TIE-2 ligand 1 (Lane L1) but not by TIE-2 ligand 2 (Lane L2) or control (Mock).

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 µg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in example 1. The results are shown in FIG. 7. Phosphotyrosine levels on the TIE-2 receptor (TIE-2-R) were induced by treatment of HEAC cells with TIE-2 ligand 1 (Lane L1) but not by TIE-2 ligand 2 (Lane L2) conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Figure 8:
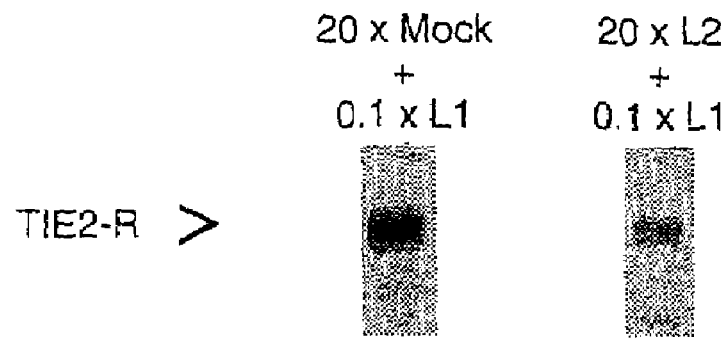
FIG. 8—Western blot showing that prior treatment of HAEC cells with excess TIE-2 ligand 2 (Lane 2) antagonizes the subsequent ability of dilute TIE-2 ligand 1 to activate the TIE-2 receptor (TIE2-R) as compared with prior treatment of HAEC cells with MOCK medium (Lane 1).

Semi-confluent HAEC cells were serum-starved as described above and then incubated for 3 min., at 37° C. with 1–2 ml. of 20×COS/JFE14-TL2 conditioned medium. Control plates were treated with 20×COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20×COS/JFE14-TL1 medium diluted to 2×, 0.5×, 0.1×, or 0.02× by addition of 20×COS/JFE14-alone medium. An assay of the initial 20×TL1 and 20×TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot, shown in FIG. 8, indicate that when compared to prior treatment of HAEC cells with MOCK medium (lane 1), prior treatment of HAEC cells with excess TIE-2 ligand 2 (lane 2) antagonizes the subsequent ability of dilute TIE-2 ligand 1 to activate the TIE-2 receptor (TIE-2-R).

Figure 9:
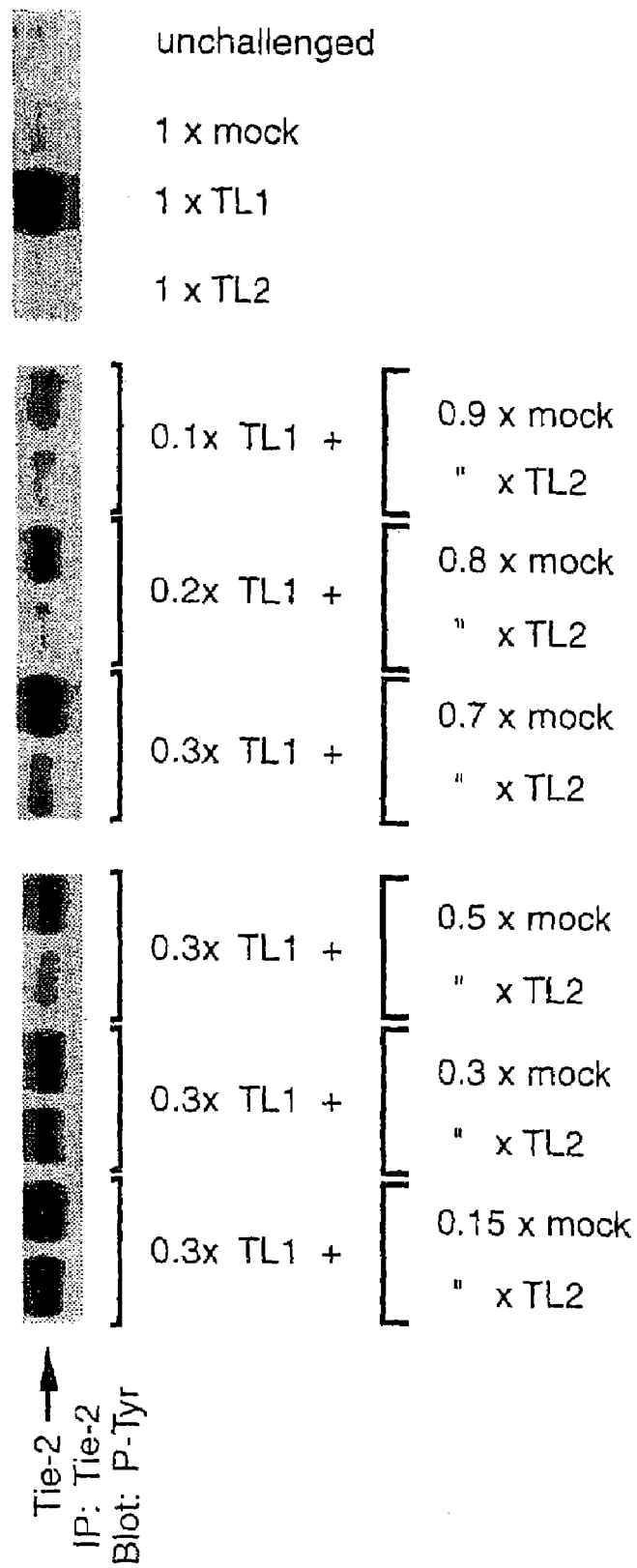
FIG. 9—Western blot demonstrating the ability of TL2 to competitively inhibit TL1 activation of the TIE-2 receptor using the human cell hybrid line, EA.hy926.

The ability of TL2 to competitively inhibit TL1 activation of the TIE-2-R was further demonstrated using the human cell hybrid line, EA.hy926 (see Example 21 for detailed description of this cell line and its maintenance). Experiments were performed in which unconcentrated COS cell media containing TL1 were mixed at varying dilutions with either MOCK- or TL2-conditioned media and placed on serum-starved EA.hy926 cell monolayers for 5 minutes at 37° C. The media were then removed, the cells were harvested by lysis and TIE-2-specific tyrosine phosphorylation was examined by Western blots, as described above. FIG. 9 shows an experiment which contains three groups of treatments, as viewed from left to right. As shown in the four lanes at the left, treatment of the EA.hy926 cells with 1×COS-TL1 alone robustly activated the endogenous TIE-2-R in these cells, whereas 1×TL2 COS medium was inactive. However, mixture of TL1 with either MOCK or TL2 demonstrated that TL2 can block the activity of TL1 in a dose-dependent fashion. In the central three pairs of lanes the ratio of TL2 (or MOCK) was decreased while the amount of TL1 in the mixture was correspondingly increased from 0.1× to 0.3×. At any of these mixture ratios the TL1:TL2 lanes showed a reduced level of TIE-2-R phosphorylation compared to that of the corresponding TL1:MOCK lanes. When the amount TL1 was held steady and the amount of TL2 (or MOCK) was decreased, however (shown in the three pairs of lanes at the right), a point was reached at which the TL2 in the sample was too dilute to effectively inhibit TL1 activity. The relative amount of each ligand present in these conditioned COS media could be estimated from their binding units as measured by the BIAcore assay and from Western blots of the COS media with ligand-specific antibodies. Consequently, we can infer that only a few-fold molar excess of TL2 is required to effectively block the activity of TL1 in vitro. This is significant because we have observed distinct examples in vivo (see Example 17 and FIG. 16) where TL2 mRNAs achieve considerable abundance relative to those of TL1. Thus, TL2 may be serving an important physiological role in effectively blocking signaling by the TIE-2-R at these sites.

Taken together these data confirm that, unlike TL1, TL2 is unable to stimulate endogenously expressed TIE-2-R on endothelial cells. Furthermore, at a few fold molar excess TL2 can block TL1 stimulation of the TIE-2 receptor, indicating that TL2 is a naturally occurring TIE-2 receptor antagonist.

EXAMPLE 10

Identification of TIE-2-Specific Binding Activity in Conditioned Medium and COS Cell Supernatants Binding activity of 10×CCM from the cell lines C2C12-ras, Rat2 ras, SHEP, and T98G, or COS cell supernatants after transfection with either human TIE-2 ligand 1 (hTL1) or human TIE-2 ligand 2 (hTL2) was measured using biosensor technology (BIAcore; Pharmacia Biosensor, Piscataway, N.J.) which monitors biomolecular interactions in real-time via surface plasmon resonance (SPR). Purified rat or human TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 μg/mL, pH 4.5) and deactivation of unreacted sites with 1.0 M ethanolamine (pH 8.5). In general, 9000–10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 μm filter (Millipore; Bedford, Mass.). Dextran (2 mg/ml) and P20 surfactant (0.005%) were added to each sample. Aliquots of 40 μL were injected across the immobilized surface (either rat or human TIE-2) at a flow rate of 5 μL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-μL pulse of 3 M $MgCl_2$.

Figure 10:
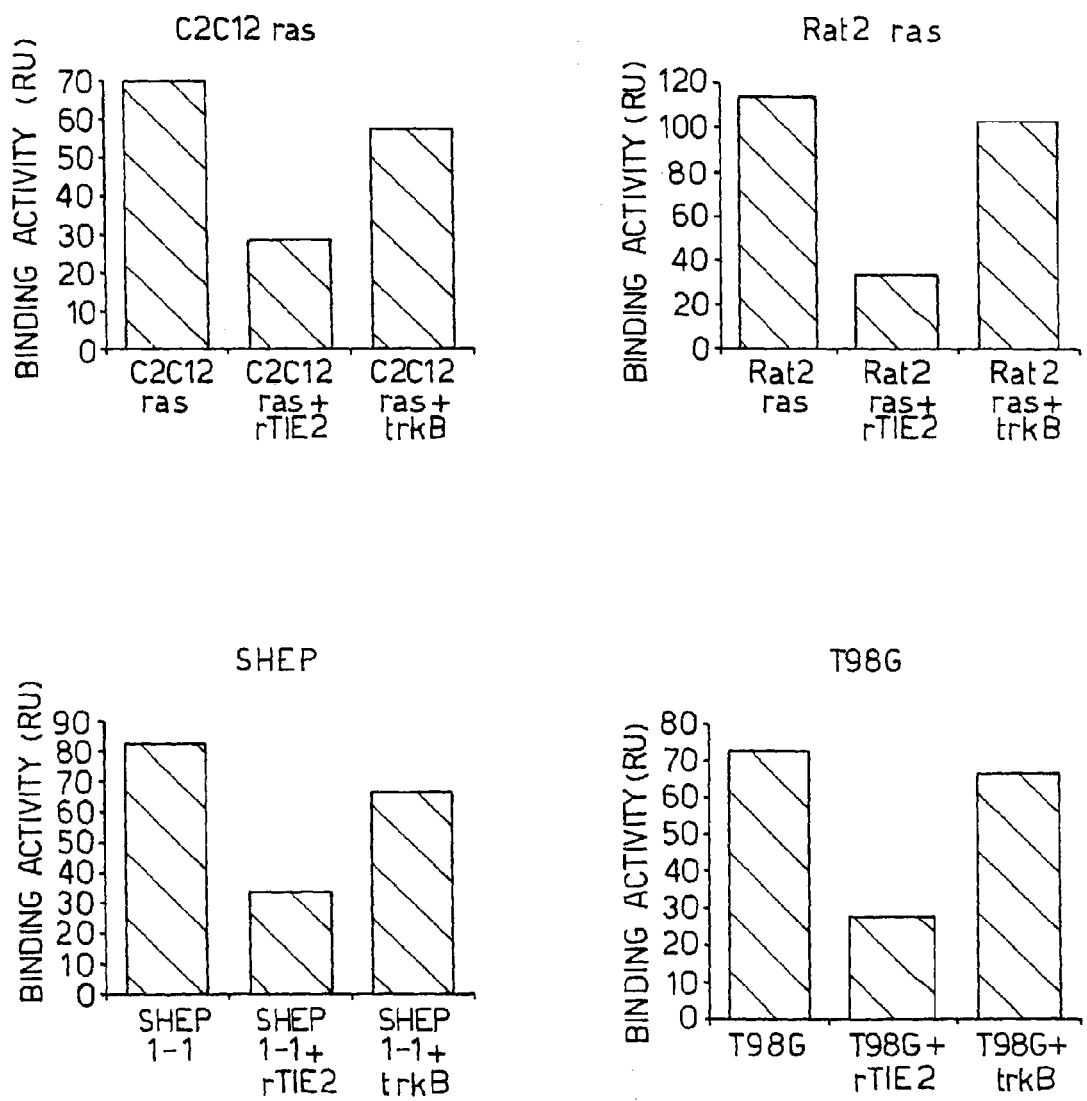
FIG. 10—Histogram representation of binding to rat TIE-2 IgG immobilized surface by TIE-2 ligand in C2C12 ras, Rat2 ras, SHEP, and T98G concentrated (10×) conditioned medium. Rat TIE-2 (rTIE2) specific binding is demonstrated by the significant reduction in the binding activity in the presence of 25 μg/ml soluble rat TIE-2 RB as compared to a minor reduction in the presence of soluble trkB RB.

The CCM samples (C2C12-ras, Rat2-ras, SHEP, T98G) were tested on the rat TIE-2 RB immobilized surface, while the recombinant hTL1 and hTL2 were tested on the human TIE-2 RB immobilized surface. In each case, specific binding to the TIE-2 receptorbody was evaluated by incubating the samples with 25 μg/ml of either soluble TIE-2 (rat or human) RB or trkB RB prior to assaying the binding activity. As shown in FIGS. 10 and 11, the addition of soluble trkB RB causes a slight decrease in the TIE-2 binding activity, while the addition of soluble TIE-2 RB significantly reduces the binding activity as compared to that measured in the absence of TIE-2 RB.

EXAMPLE 11

TIE-2 RB Specifically Blocks Activation of the TIE-2 Receptor by TIE-2 Ligand 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE-2- or TrkB-RB and then compared for their ability to activate TIE-2 receptors naturally present in a human endothelial cell line.

Conditioned COS media were generated from COS-7 cells transfected with either the pJFE14 expression vector alone (MOCK), or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Figure 12:
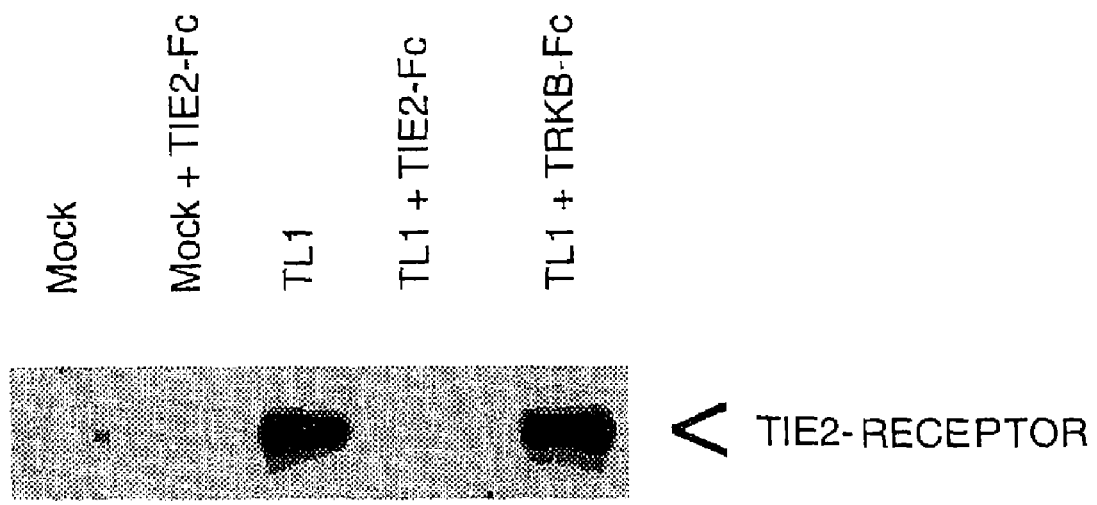
FIG. 12—Western blot showing that TIE-2 receptorbody (denoted TIE-2 RB or, as here, TIE2-Fc) blocks the activation of TIE-2 receptors by TIE-2 ligand 1 (TL1) in HUVEC cells, whereas an unrelated receptorbody (TRKB-Fc) does not block this activation.

Northern (RNA) analyses revealed significant levels of tie-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE-2- or TrkB-RBs to COS media containing TL1. HUVEC cells were maintained at 37° C., 5% $CO_2$ in a complete endothelial cell growth medium (Clonetics, Inc.) that contained 5% fetal bovine serum, soluble bovine brain extract with 10 μg/ml heparin, 10 ng/ml human EGF, 1 ug/ml hydrocortisone, 50 μg/ml gentamicin and 50 ng/ml amphotericin-B. Assessment of whether TL1 could activate TIE-2 receptor in the HUVEC cells was done as follows. Confluent dishes of HUVEC cells were serum-starved for two-to-four hours in low-glucose Dulbecco's MEM at 37° C., 5% $CO_2$, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE-2- or TrkB-RB added to 50 μg/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1. The results are shown in FIG. 12. Phosphotyrosine levels on the TIE-2 receptor were induced by treatment of HUVEC cells with TIE-2 ligand 1 (TL1) relative to that seen with control medium (MOCK) and this induction is specifically blocked by prior incubation with TIE-2-RB (TIE-2-Fc) but not by incubation with TrkB-RB (TrkB-Fc). These data indicate that soluble TIE-2 RB can serve as a selective inhibitor to block activation of TIE-2 receptor by TIE-2 ligand 1.

EXAMPLE 12

Construction of TIE-2 Ligandbodies

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TL2-Fc was cloned as an Eco RI-NotI fragment into the baculovirus transfer plasmid pVL1393. Plasmid DNA was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 μg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 μg/mL MTT (3-[4,5-dimethylthiazol-2-yl]2, 5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1× antibiotic/antimycotic solution (Gibco BRL) and 25 mg/L Gentamicin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×106 cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTL2-Fc-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

EXAMPLE 13

Expression of TIE-1, TIE-2, TL1, and TL2 in Renal Cell Carcinoma

In situ hybridization experiments were performed on human renal cell carcinoma tumor tissue using TIE-1, TIE-2, TL1, and TL2 cDNA probes. TIE-2, TIE-1, TL1, and TL2 expression were all up-regulated in the tumor vasculature. Ligand expression appeared to be localized to either the vascular endothelial cells (TL2) or very near the vascular endothelial cells in the mesenchyme (TL1). VEGF has been shown to be dramatically up-regulated in this tumor tissue. Brown, et al. Am. J. Pathol. 143:1255–1262 (1993).

EXAMPLE 14

Expression of TIE-1, TIE-2, TL1, and TL2 in Wound Healing

In situ hybridization experiments were performed on cross-sectional tissue slices obtained from a rat cutaneous wound model using TIE-1, TIE-2, TL1, and TL2 cDNA probes. The wound healing model involves pressing a small cork bore against the skin of a rat and removing a small, cylindrical plug of skin. As healing begins at the base of the wound, a vertical slice of tissue is taken and used for in situ hybridization. In the tested tissue sample, TL1 and TL2 appeared to be slightly up-regulated by four days post-injury. In contrast to the slightly up-regulated expression of TL1 and TL2 in this tissue, VEGF expression, which may precede TL1 and TL2 expression, is dramatically up-regulated.

EXAMPLE 15

Expression of TIE Ligands in Fetal Liver and Thymus

Figure 13:
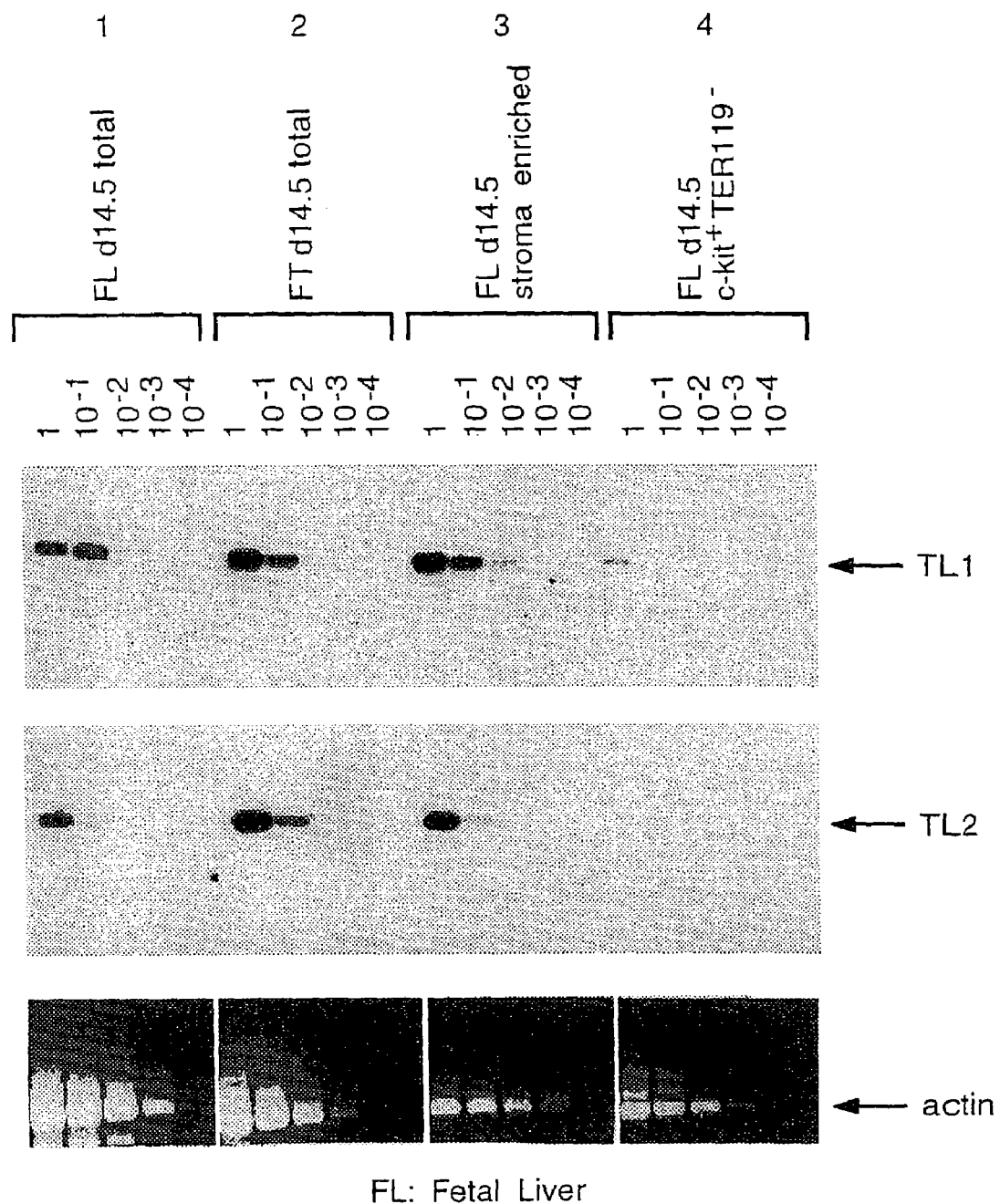
FIG. 13—Agarose gels showing serial dilutions [undiluted (1) to $10^{-4}$] of the TL1 and TL2 RT-PCR products obtained from E14.5 mouse fetal liver (Lanes 1—total, Lanes 3—stromal enriched, and Lanes 4—c-kit+TER119 hematopoietic precursor cells) and E14.5 mouse fetal thymus (Lanes 2—total).
Figure 14:
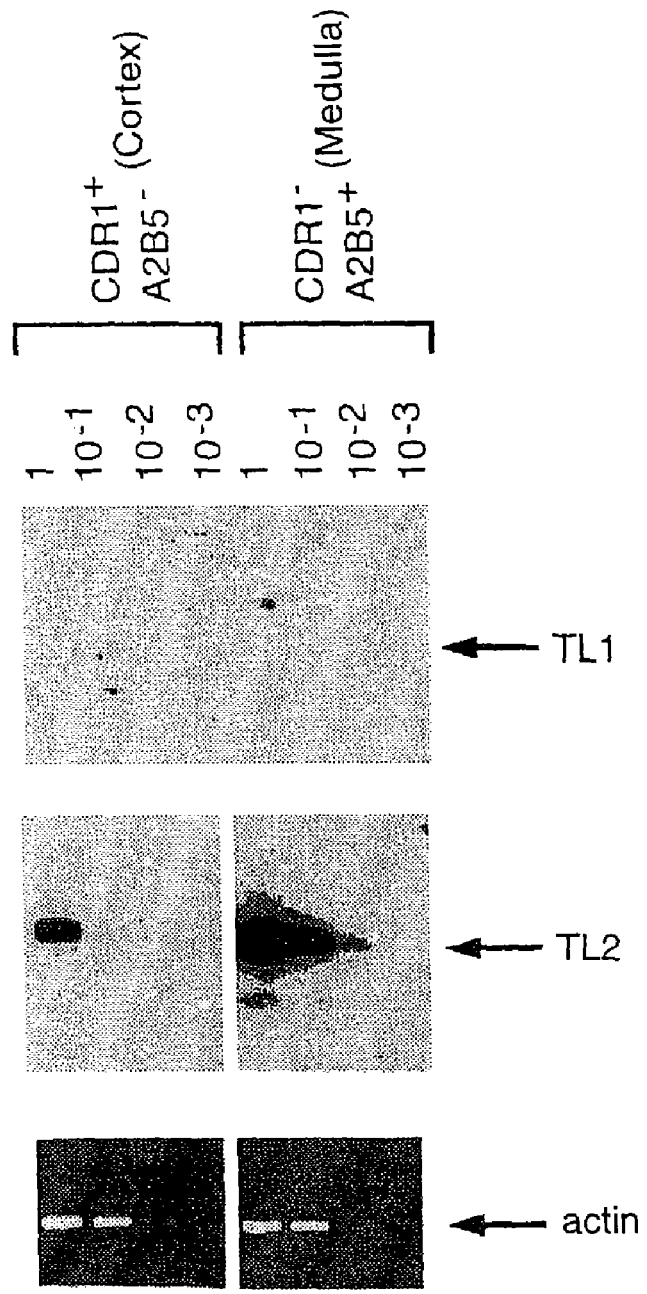
FIG. 14—Agarose gels showing serial dilutions [undiluted (1) to $10^{-3}$] of the TL1 and TL2 RT-PCR products obtained from E17.5 mouse fetal thymus cortical stromal cells (Lanes 1—CDR1+/A2B5−) and medullary stromal cells (Lane CDR1−/A2B5+).

Reverse transcription-PCR (RT-PCR) was performed on mouse E14.5 fetal liver and mouse E17.5 fetal thymus. Agarose gel electrophoresis of the RT-PCR products revealed that in the mouse fetal liver, TIE-2 ligand 1 (TL1) RNA is enriched in the stromal region, but is absent in c-kit+TER119 hematopoietic precursor cells. In this same tissue, TIE-2 ligand 2 (TL2) RNA is enriched in the stromal cells, but absent in the hematopoietic precursor cells (FIG. 13). In the mouse fetal thymus, TL2 is enriched in the stromal cells (FIG. 14).

EXAMPLE 16

The TIE Receptor/Ligand System in Angiogenesis

Although the TIE-2/TIE ligand system appears to play an important role in endothelial cell biology, it has not been shown to play a significant, active role in the early to intermediate stages of vascularization (e.g. angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

Figure 15:
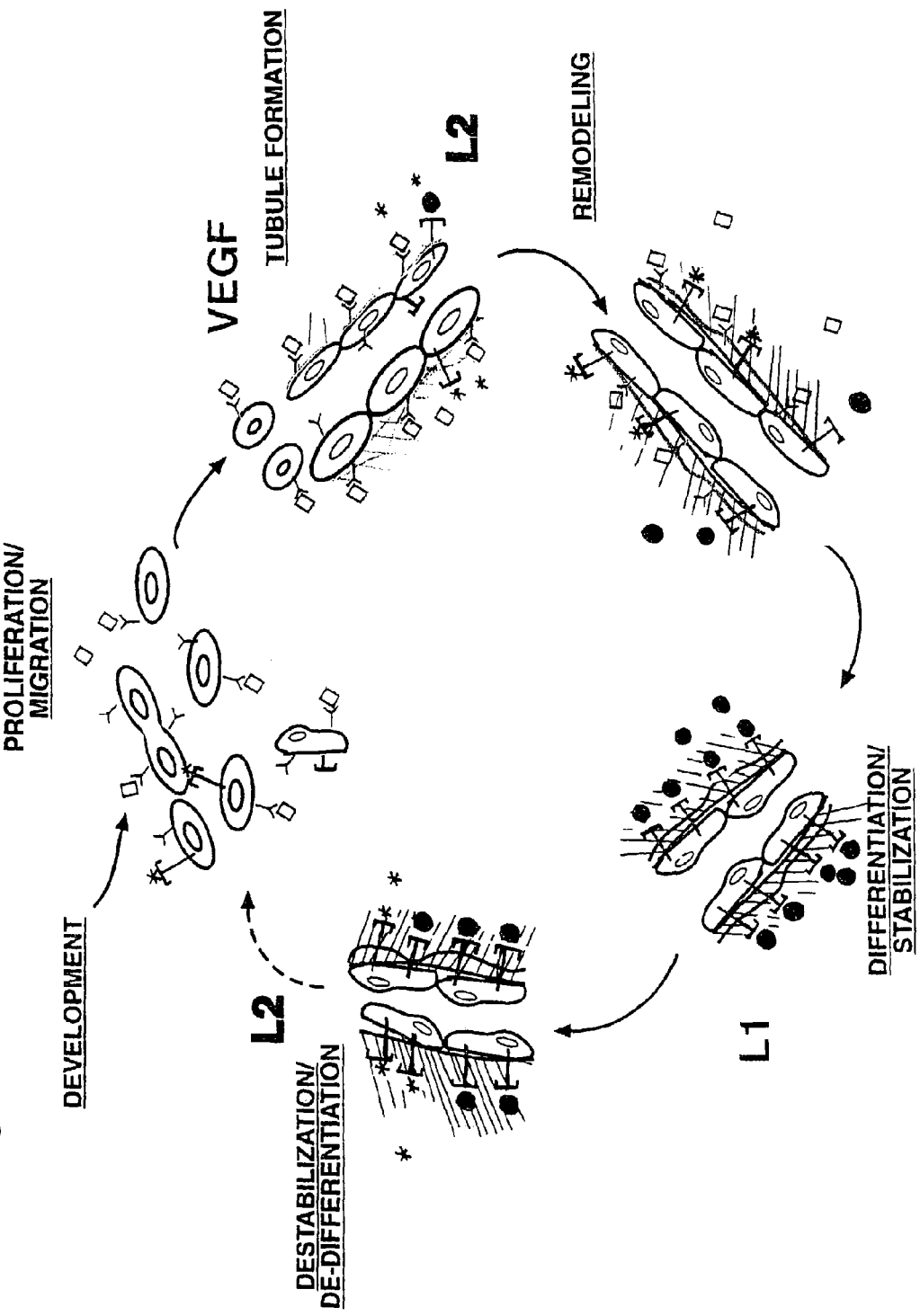
FIG. 15—A schematic representation of the hypothesized role of the TIE-2/TIE ligands in angiogenesis. TL1 is represented by (●), TL2 is represented by (*), TIE-2 is represented by (T), VEGF is represented by ([ ]), and flk-1 (a VEGF receptor) is represented by (Y).

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (e.g. de-stabilization/de-differentiation of mature endothelial cells allowing the formation of new vessels from existing vasculature, inhibition of inappropriate blood vessel formation, and regression/involution of mature blood vessels). FIG. 15 is a schematic representation of the hypothesized role of the TIE-2/TIE ligands in angiogenesis. In this figure TL1 is represented by (●), TL2 is represented by (*), TIE-2 is represented by (T), VEGF is represented by ([ ]), and flk-1 (a VEGF receptor) is represented by (Y).

EXAMPLE 17

Figure 16:
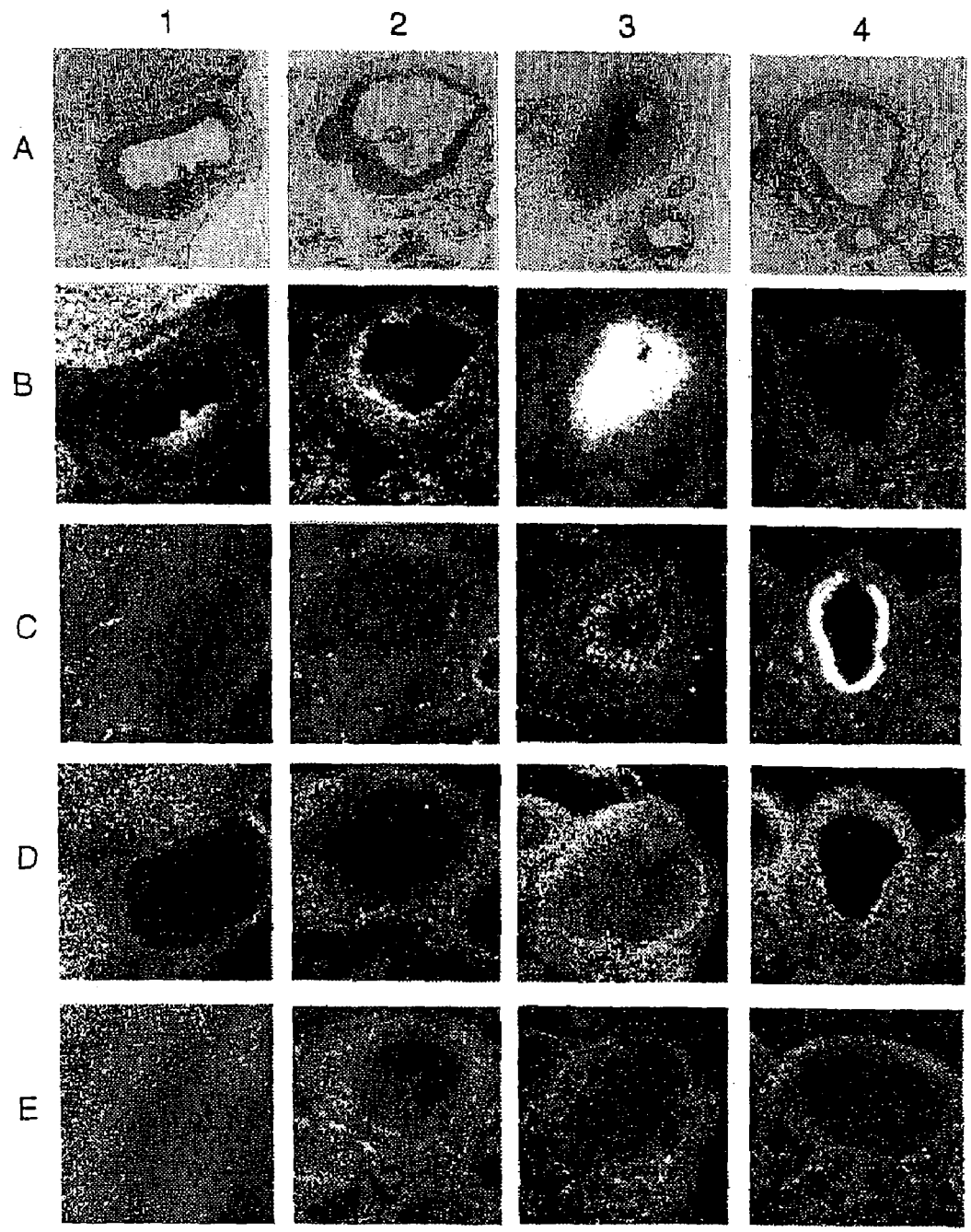
FIG. 16—In situ hybridization slides showing the temporal expression pattern of TIE-2, TL1, TL2, and VEGF during angiogenesis associated with follicular development and corpus luteum formation in the ovary of a rat that was treated with pregnant mare serum. Column 1: Early pre-ovulatory follicle; Column 2: pre-ovulatory follicle; Column 3: early corpus luteum; and Column 4: atretic follicle; Row A: bright field; Row B: VEGF; Row C: TL2; Row D: TL1 and Row E: TIE-2 receptor.

Expression of TIE Ligands in the Female Reproductive System: Expression in the Ovary Preliminary observations made in experiments examining the expression of the TIE receptors and ligands in the female reproductive system are consistent with the hypothesis the TL1 plays a role in neovascularization which temporally follows that of VEGF. The pattern of TL2 expression is also consistent with an antagonism of the action of TL1, and a specific role in vascular regression. To verify this, expression of relevant mRNAs can be examined following experimental induction of follicular and luteal development so that their temporal relation to various aspects of neovascularization/vascular regression can be more clearly defined (e.g. in conjunction with endothelial cell staining, vascular fills). Angiogenesis associated with follicular development and corpus luteum formation in staged ovaries of mature, female rats or following induced ovulation in pre-pubertal animals was followed using in situ hybridization. FIG. 16 contains photographs of in situ hybridization slides showing the temporal expression pattern of TIE-2, TL1, TL2, and VEGF during the ovarian cycle [Column 1: Early pre-ovulatory follicle; Column 2: pre-ovulatory follicle; Column 3: early corpus luteum; and Column 4: atretic follicle; Row A: bright field; Row B: VEGF; Row C: TL2; Row D: TL1 and Row E: TIE-2 receptor]. These studies revealed that VEGF, TL1 and TL2 are expressed in a temporally and spatially coordinate fashion with respect to the development and regression of vasculature in the ovary, specifically with respect to the establishment of the vascular system which is generated in the course of the conversion of an ovarian follicle to a corpus luteum (CL).

Briefly, VEGF expression increases in the follicular granule layer prior to its vascularization during the process of luteinization. During the process of CL formation, highest levels of VEGF expression are apparent in the center of the developing CL in the vicinity of luteinizing cells which are not yet vascularized. VEGF levels remain moderately high and are diffusely distributed in the developed CL. In contrast, noticeably enhanced expression of TIE-2 ligand 1 occurs only late in process of CL formation, after a primary vascular plexus has been established. Later, TL1 expression is apparent throughout the CL at which time the definitive capillary network of the CL has been established.

TL2 exhibits a more complex pattern of expression than either VEGF or TL1. In the developing CL, TL2 is expressed at highest levels at the front of the developing capillary plexus—between the central avascular region of the CL where VEGF expression is highest, and the most peripheral portion of the CL where TL1 expression is dominant and where the luteinization process is complete and the vascular system is most mature. TL2 also appears to be expressed at high levels in the follicular layer of large follicles which are undergoing atresia. While TL1 is also apparent in atretic follicles, VEGF is not expressed.

The pattern of expression described above is most consistent with a role for VEGF in the initiation of angiogenesis, with TL1 acting late in this process—for example in modeling and/or stabilization of the definitive vascular network. In contrast, TL2 is present both in areas of active expansion of a newly forming vascular network (during CL formation), and in regions which fail to establish a new vasculature and vascular regression is in progress (atretic follicles). This suggests a more dynamic and complex role for TL2, possibly involving destabilization of existing vasculature (necessary for regression) or developing vasculature (necessary for the dynamic modeling of newly forming vessels).

EXAMPLE 18

Construction and Characterization of the CYS-TL1 Mutant

Figure 17:
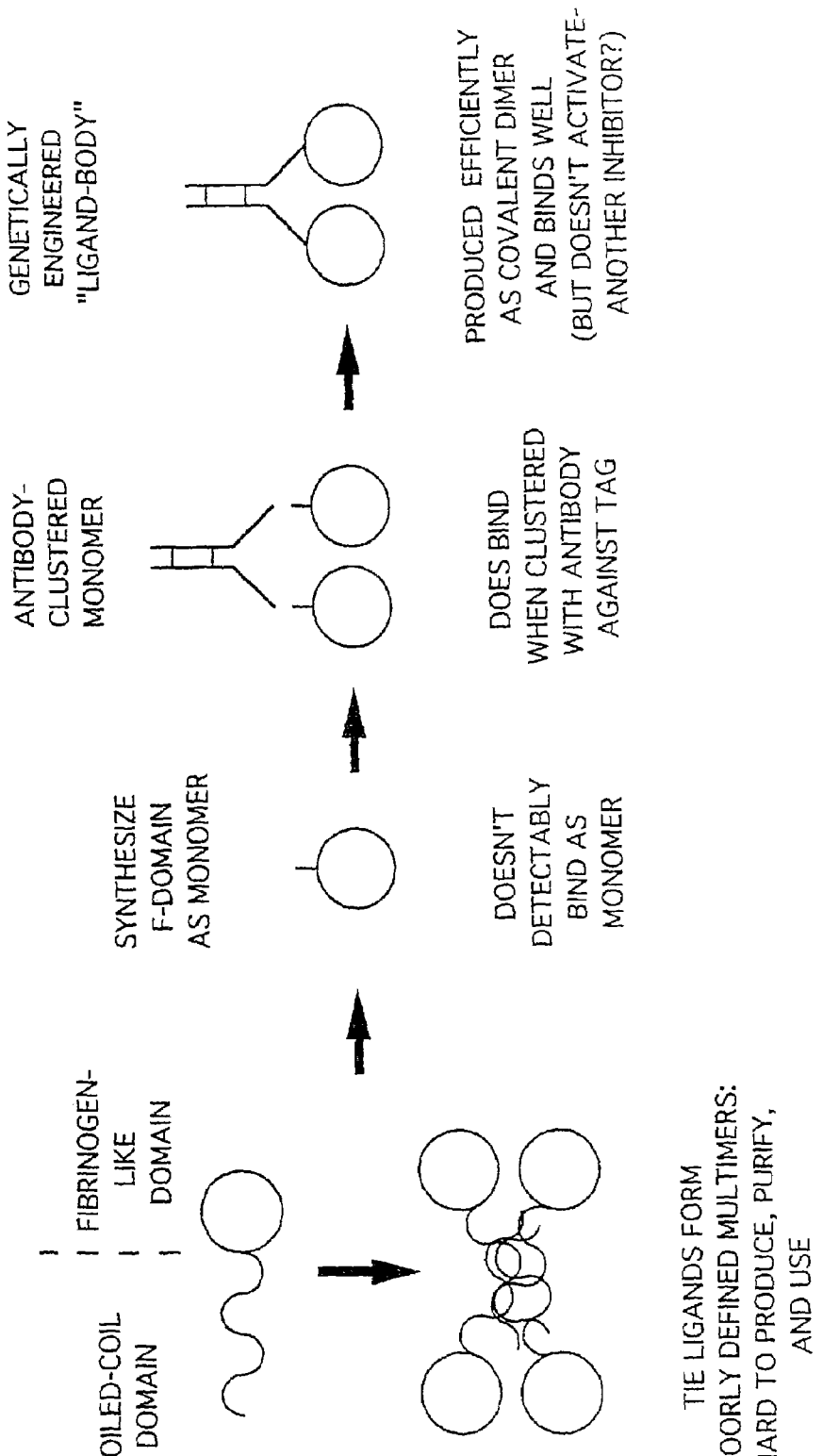
FIG. 17—Diagrammatic representation of the TIE-2 ligands, showing the "coiled coil" and fibrinogen-like domains and the engineering of multimers of the fibrinogen-like domains using antibodies to myc-tags as well as Fc tagging.
Figure 18:
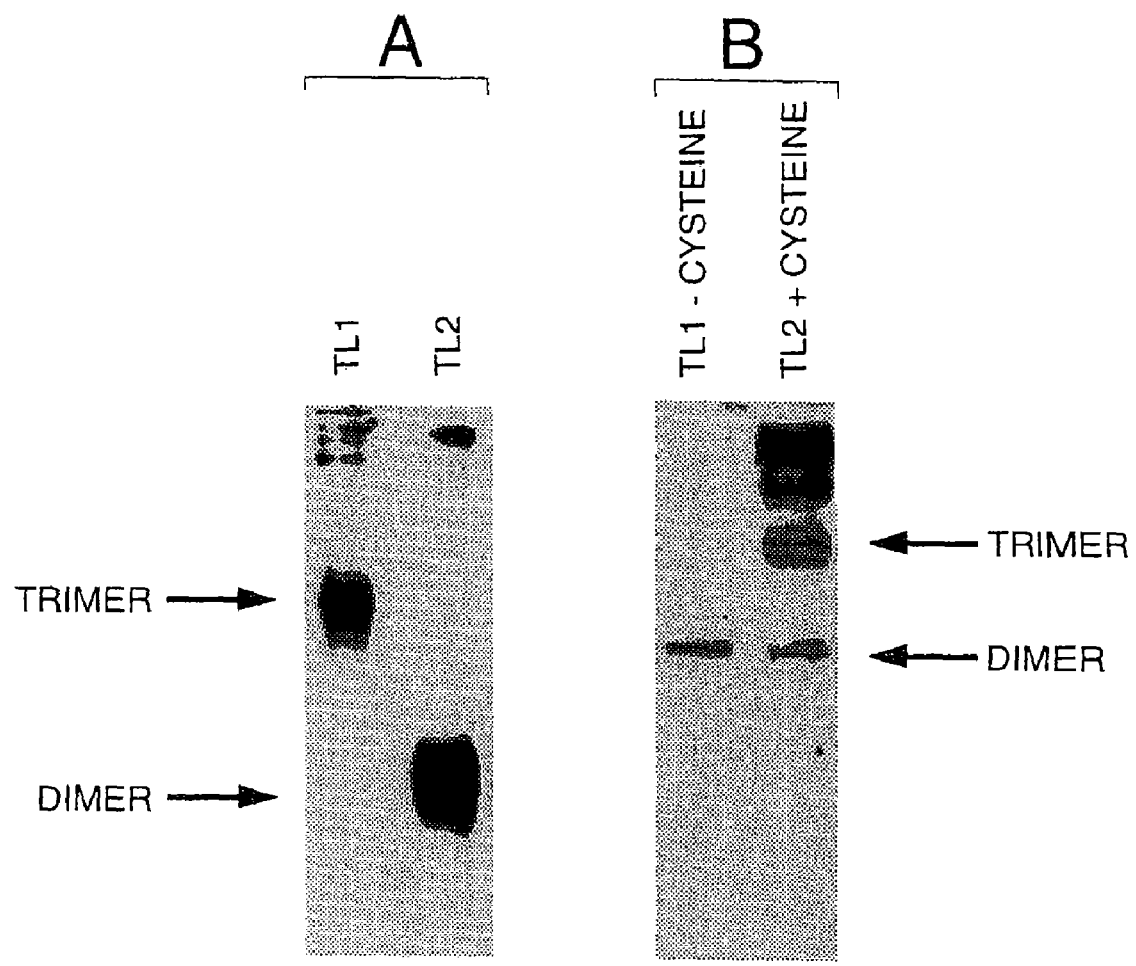
FIG. 18—Western blot of the covalent multimeric structure of TL1 and TL2 (Panel A) and the interconversion of TL1 and TL2 by the mutation of one cysteine (Panel B).

The TIE-2 ligands have two major structural domains, one described as a "coiled-coil" domain comprising the approximate C-terminal third of the protein and the other a "fibrinogen-like" domain comprising the approximate N-terminal two-thirds of the protein. Although the TIE-2 ligands, designated TL1 and TL2, share similar structural homology, they exhibit different physical and biological properties. Under non-reducing electrophoretic conditions, both proteins exhibit covalent, multimeric structures, with TL1 existing primarily as a trimer and TL2 existing primarily as a dimer. FIG. 17 is a schematic representation of how the TIE-2 ligands may be interacting to form multimers. In terms of biological activity, TL1 has been shown to be an agonist of the TIE-2 receptor, as demonstrated by induction of phosphorylation in TIE-2 expressing cells. TL2, on the other hand, appears to be a competitive inhibitor of TL1. Investigations into what factors might be contributing to the different physical and biological properties of the two molecules revealed the presence of a cysteine residue (CYS265) preceding the fibrinogen-like domain in TL1 but absent in TL2. This CYS265 residue in TL1 is encoded by TGC and is located at about nucleotides 1102–1104 at the approximate junction between the coiled-coil and fibrinogen-like domains. Because cysteine residues are generally involved in disulfide bond formation, the presence of which can contribute to both the tertiary structure and biological properties of a molecule, it was thought the perhaps the presence of the CYS265 in TL1 might be at least partially responsible for the different properties of the two molecules. To test this hypothesis, an expression plasmid was constructed which contained a mutation in TL1 in which the CYS was replaced with an amino acid which does not form disulfide bonds. In addition to this TL1/CYS− mutant, a second expression plasmid was constructed which mutated the corresponding position in TL2 so that this residue was now a cysteine. Both non-mutated and mutated expression plasmids of TL1 and TL2 were transiently transfected into COS cells. Cell supernatants containing the recombinant proteins were harvested and samples subjected to both reducing and non-reducing SDS/PAGE electrophoresis and subsequent western blotting. FIG. 18 contains western blots of both non-mutated and mutated TL1 and TL2 proteins under revealing that the TL1/CYS− mutant behaves more TL2-like in that it runs as a dimer and that the TL2/CYS+ mutant behaves more TL1-like in that it is able to form a trimer as well as higher-order multimers. Interestingly, when the two mutant proteins were tested for their ability to induce phosphorylation in TIE-2 expressing cells, the TL1/CYS− mutant was able to activate the TIE-2 receptor, whereas the TL2/CYS+ mutant did not gain any activating activity.

EXAMPLE 19

Construction and Characterization of Fibrinogen-Like Domain Only Mutants

In order to test whether the fibrinogen-like domain (F-domain) of the TIE-2 ligands contained TIE-2 activating activity, expression plasmids were constructed which deleted the coiled-coil domain, leaving only that portion of the DNA sequence encoding the F-domain (beginning at about nucleotide 1159, amino acid residue ARG284). This mutant construct was transiently transfected into COS cells. The supernatant containing the recombinant protein was harvested. The TL1/F-domain mutant was tested for it's ability to bind the TIE-2 receptor. The results showed that, as a monomer, the TL1/F-domain mutant was not able to bind TIE-2 at a detectable level. However, when the TL1/F-domain monomer was myc-tagged and subsequently clustered with an antibody directed against the myc tag, it did exhibit detectable binding to TIE-2. However, the antibody-clustered TL1/F-domain mutant was not able to induce phosphorylation in a TIE-2 expressing cell line. FIG. 17 shows a schematic representation of the F-domain construct and its binding ability plus and minus antibody clustering.

EXAMPLE 20

A Receptorbody Binding Assay and a Ligand Binding and Competition Assay

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific anti-human Fc antibody which is alkaline phosphatase tagged. Excess reporter antibody is washed away, then the AP reaction is developed using a colored substrate. The assay is quantitated using a spectrophotometer. FIG. 19 shows a typical TIE-2-IgG binding curve. This assay has been used to evaluate the integrity of TIE-2-IgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 20 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

EXAMPLE 21

EA.hy926 Cell Line can be Used as a Reporter Cell Line for TIE Ligand Activity

EA.hy926 is a cell hybrid line that was established by fusion of HUVEC with the human lung carcinoma-derived line, A549 Edgell, et al. Proc. Natl. Acad. Sci. (USA) 80, 3734–3737 (1983). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1× hypoxanthine-aminopterin-thymidine (HAT, Gibco/BRL). After three to four days of growth, the cells are passaged once again at $1.5 \times 10^6$ cells per T-75 flask and cultured an additional three to four days. For phosphorylation assays, cells prepared as described above were serum-starved by replacement of the culture medium with high-glucose DMEM and incubation for 2–3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 mM NaCl, 50 mM NaF, 1mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

Deposits

The following have been deposited with the American Type Culture Collection, 12301 Parklawn Drive, Rockville, Md. 20852 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding TIE-2 receptorbody was deposited with the ATCC on Oct. 7, 1994 and designated as "vTIE-2 receptorbody" under ATCC Accession No. VR2484. A lambda phage vector containing human tie-2 ligand DNA was deposited with the ATCC on Oct. 26, 1994 and designated as λgt10 encoding htie-2 ligand 1 under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963.

The present invention is not to be limited in scope by the specific-embodiments described herein. Indeed, various modifications of the invention in addition to those described herein will become apparent to those skilled in the art from the foregoing description and accompanying figures. Such modifications are intended to fall within the scope of the appended claims.

The invention claimed is:

1. An isolated nucleic acid molecule comprising a nucleotide sequence selected from the group consisting of:
   (a) a nucleotide sequence encoding the fibrinogen-like domain of human TIE-2 ligand consisting of nucleotides 1197–1844 of SEQ ID NO: 5, and
   (b) a nucleotide sequence which, due to the degeneracy of the genetic code, differs from the nucleotide sequence of (a) and which encodes the fibrinogen-like domain of human TIE-2 ligand, said fibrinogen-like domain of human TIE-2 ligand consisting of amino acids 281–496 of SEQ ID NO:6.

2. A vector which comprises a nucleic acid molecule of claim 1.

3. An isolated vector according to claim 2, wherein the nucleic acid molecule is operatively linked to an expression control sequence that directs its expression in a host cell.

4. An isolated vector according to claim 2, which is a plasmid.

6. An isolated non-human host-vector system according to claim 5, wherein the host cell is a bacterial, yeast, insect or mammalian cell.

7. A method of producing a polypeptide which comprises growing cells of the host-vector system of claim 6, under conditions permitting production of the polypeptide and recovering the polypeptide so produced.

8. The nucleic acid molecule of claim 1 further comprising a nucleic acid sequence encoding an immunoglobulin constant region.

9. The nucleic acid molecule of claim 8, wherein the immunoglobulin constant region is the Fc portion of human IgG1.

* * * * *